United States Patent
Corgie

(10) Patent No.: US 11,517,014 B2
(45) Date of Patent: Dec. 6, 2022

(54) MAGNETICALLY IMMOBILIZED MICROBIOCIDAL ENZYMES

(71) Applicant: ZYMtronix, LLC, Ithaca, NY (US)

(72) Inventor: Stephane Corgie, Ithaca, NY (US)

(73) Assignee: ZYMtronix, Inc., Ithaca, NY (US)

( * ) Notice: Subject to any disclaimer, the term of this patent is extended or adjusted under 35 U.S.C. 154(b) by 32 days.

(21) Appl. No.: 16/865,156

(22) Filed: May 1, 2020

(65) Prior Publication Data

US 2020/0315167 A1 Oct. 8, 2020

Related U.S. Application Data

(62) Division of application No. 15/572,306, filed as application No. PCT/US2016/031419 on May 9, 2016, now Pat. No. 10,881,102.

(60) Provisional application No. 62/215,713, filed on Sep. 8, 2015, provisional application No. 62/163,032, filed on May 18, 2015.

(51) Int. Cl.
| | | |
|---|---|---|
| *A01N 25/14* | (2006.01) | |
| *C12N 11/18* | (2006.01) | |
| *C12N 9/00* | (2006.01) | |
| *C12N 11/14* | (2006.01) | |
| *A01N 59/00* | (2006.01) | |
| *A01N 63/50* | (2020.01) | |
| *A61P 31/12* | (2006.01) | |
| *A61P 31/04* | (2006.01) | |
| *B82Y 5/00* | (2011.01) | |

(52) U.S. Cl.
CPC ............. *A01N 25/14* (2013.01); *A01N 59/00* (2013.01); *A01N 63/50* (2020.01); *A61P 31/04* (2018.01); *A61P 31/12* (2018.01); *C12N 9/00* (2013.01); *C12N 11/14* (2013.01); *C12N 11/18* (2013.01); *B82Y 5/00* (2013.01)

(58) Field of Classification Search
CPC ........ A01N 59/00; A01N 63/50; A01N 25/14; A61L 15/38; A61L 15/42; A61L 2300/11; A61P 31/04; B82Y 5/00
See application file for complete search history.

(56) References Cited

U.S. PATENT DOCUMENTS

| | | | |
|---|---|---|---|
| 4,152,210 A | 5/1979 | Robinson et al. | |
| 5,460,830 A | 10/1995 | Kossovsky et al. | |
| 5,965,418 A | 10/1999 | Fuglsang et al. | |
| 6,440,711 B1 | 8/2002 | Dave et al. | |
| 6,447,811 B1 | 9/2002 | Ravensberg et al. | |
| 7,241,883 B2 | 7/2007 | Lugade et al. | |
| 7,385,053 B2 | 6/2008 | Lugade et al. | |
| 7,459,145 B2 | 12/2008 | Bao et al. | |
| 7,485,367 B2 | 2/2009 | Chen et al. | |
| 7,731,954 B2 | 6/2010 | Davis et al. | |
| 8,075,793 B2 | 12/2011 | Moreira et al. | |
| 8,188,269 B1 | 5/2012 | Lugade et al. | |
| 8,841,105 B2 | 9/2014 | Sakai et al. | |
| 8,940,179 B2 | 1/2015 | Suh et al. | |
| 9,035,003 B2 | 5/2015 | Hanson et al. | |
| 9,597,672 B2 | 3/2017 | Corgie et al. | |
| 9,765,324 B2 | 9/2017 | Corgie et al. | |
| 10,260,061 B2 | 4/2019 | Corgie | |
| 10,316,313 B2 | 6/2019 | Corgie | |
| 10,351,841 B2 | 7/2019 | Corgie | |
| 2003/0138490 A1 | 7/2003 | Hu et al. | |
| 2003/0146529 A1 | 8/2003 | Chen et al. | |
| 2003/0203056 A1 | 10/2003 | Tumbers | |
| 2004/0039201 A1 | 2/2004 | Lugade et al. | |
| 2004/0043135 A1 | 3/2004 | Han et al. | |
| 2004/0166547 A1 | 8/2004 | Sullivan et al. | |
| 2006/0034816 A1 | 2/2006 | Davis | |
| 2006/0127461 A1 | 6/2006 | Bloor | |
| 2006/0165910 A1 | 7/2006 | Kodas et al. | |
| 2006/0286379 A1 | 12/2006 | Gao et al. | |
| 2006/0289354 A1* | 12/2006 | Zhou | A01N 63/50 424/94.4 |
| 2007/0135312 A1 | 6/2007 | Melbouci | |
| 2007/0154565 A1 | 7/2007 | Zaghmout | |
| 2008/0103061 A1 | 5/2008 | Lugade et al. | |
| 2008/0287288 A1 | 11/2008 | Ying et al. | |
| 2008/0305048 A1 | 12/2008 | Josephson et al. | |

(Continued)

FOREIGN PATENT DOCUMENTS

| | | |
|---|---|---|
| CN | 1580233 A | 2/2005 |
| CN | 101109016 A | 1/2008 |

(Continued)

OTHER PUBLICATIONS

Supplementary European Search Report dated Sep. 29, 2016 issued in EP 13 84 4083.9.
Supplementary Partial European Search Report dated Apr. 29, 2016 issued in EP 13844083.9.
Ping, Z. et al., "Research and application of magnetic fluidized bed", Chemical Industry and Engineering Progress, (Apr. 25, 2006), pp. 371-377, with English absttract.
Chinese Office Action dated Mar. 23, 2016 issued in corresponding Chinese Patent Application No. 201380063389.8 with English-language translation.
Abdullah M. et al., "Preparation of Oxide Particles with Ordered Macropores by Colloidal Templating and Spray Pyrolysis", Acta Materialia 52:5151-5156 (2004).

(Continued)

*Primary Examiner* — Mark V Stevens
(74) *Attorney, Agent, or Firm* — Kaplan IP Law, PC; Jonathan M. Kaplan

(57) ABSTRACT

The present invention provides compositions and methods for reducing microbial contamination or infection in plants, animals, fabrics, and products therefrom. The present invention also provides compositions and methods for reducing human infections. In particular, it provides solid magnetic nanoparticles comprising bacteriostatic, bactericidal, fungistatic, or fungicidal enzymes in one component, and substrates for the enzymes in another component. The compositions are dormant and become active upon exposure to hydration and oxygen.

19 Claims, 17 Drawing Sheets

(56) References Cited

U.S. PATENT DOCUMENTS

Figure 1:
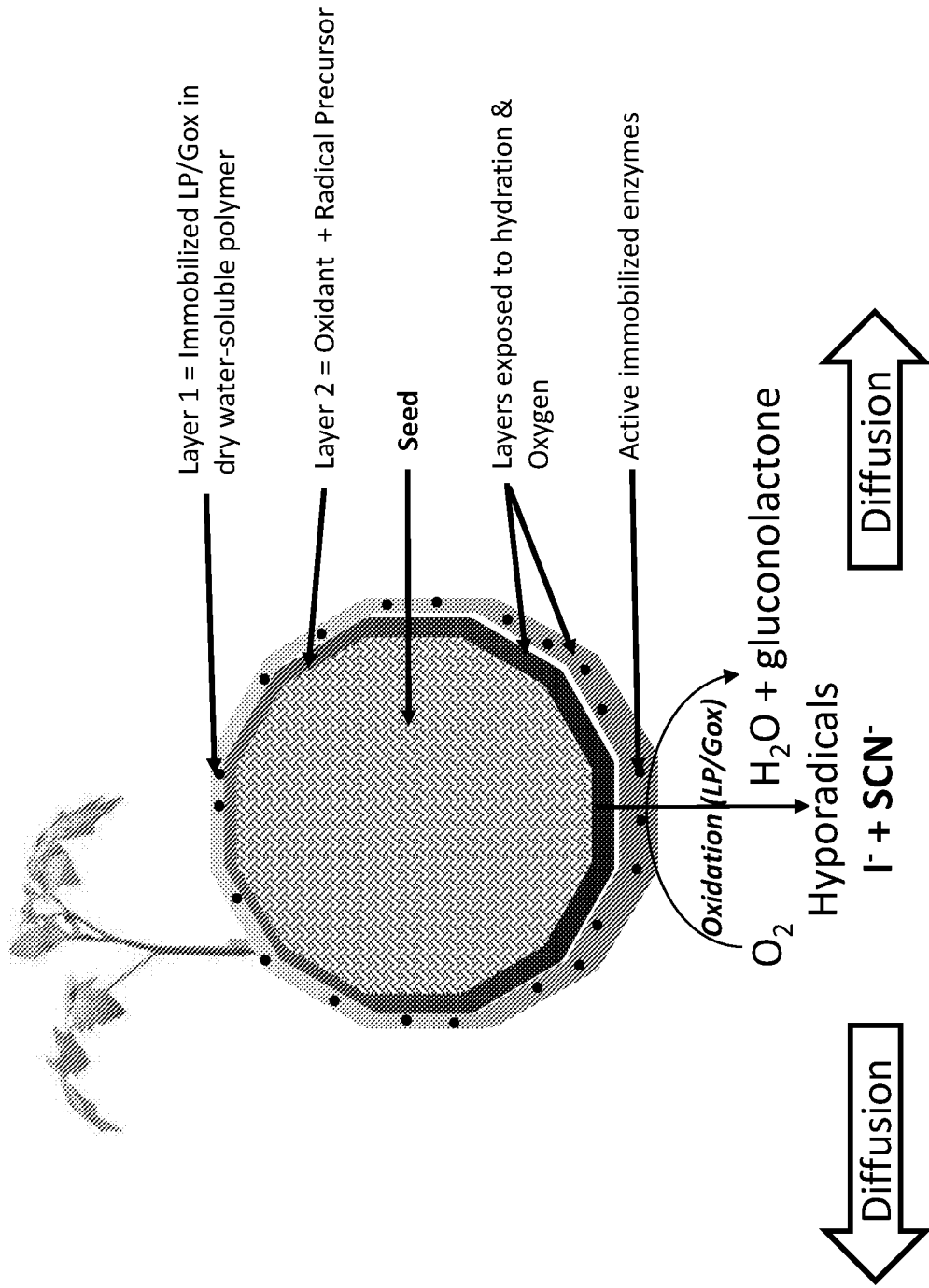

| | | |
|---|---|---|
| 2009/0053512 A1 | 2/2009 | Pyun et al. |
| 2009/0142281 A1 | 6/2009 | Rand et al. |
| 2009/0214885 A1 | 8/2009 | Her et al. |
| 2009/0238811 A1* | 9/2009 | McDaniel ............... A61L 2/00 424/94.2 |
| 2009/0285890 A1 | 11/2009 | Plas et al. |
| 2010/0056360 A1 | 3/2010 | Lee |
| 2010/0056816 A1 | 3/2010 | Wallin et al. |
| 2010/0152326 A1 | 6/2010 | Kurz |
| 2010/0226856 A1 | 9/2010 | Vitaliano et al. |
| 2010/0285376 A1 | 11/2010 | Hsueh et al. |
| 2011/0203756 A1 | 8/2011 | Nordin et al. |
| 2011/0300201 A1 | 12/2011 | Becker et al. |
| 2011/0312497 A1 | 12/2011 | Barg et al. |
| 2012/0039799 A1 | 2/2012 | Franzen et al. |
| 2012/0058074 A1 | 3/2012 | Braig et al. |
| 2012/0108491 A1 | 5/2012 | Simonsen |
| 2012/0123026 A1 | 5/2012 | Lugade et al. |
| 2012/0214218 A1 | 8/2012 | Xing et al. |
| 2012/0270031 A1 | 10/2012 | Guan et al. |
| 2013/0196407 A1 | 8/2013 | Sheldon et al. |
| 2014/0004583 A1 | 1/2014 | Corgie et al. |
| 2014/0046023 A1 | 2/2014 | Gottschall et al. |
| 2014/0100111 A1 | 4/2014 | Schultz |
| 2014/0296507 A1 | 10/2014 | Sannino et al. |
| 2014/0377789 A1 | 12/2014 | Moerman |
| 2015/0056145 A1 | 2/2015 | Chae et al. |
| 2015/0252352 A1 | 9/2015 | Corgie et al. |
| 2017/0096658 A1 | 4/2017 | Corgie et al. |
| 2017/0175101 A1 | 6/2017 | Corgie et al. |
| 2017/0189960 A1 | 7/2017 | Ibe |
| 2018/0087043 A1 | 3/2018 | Corgie |
| 2018/0146663 A1 | 5/2018 | Corgie et al. |
| 2018/0200701 A1 | 7/2018 | Corgie et al. |
| 2019/0174745 A1 | 6/2019 | Corgie |
| 2019/0174746 A1 | 6/2019 | Corgie |
| 2019/0309282 A1 | 10/2019 | Corgie |
| 2020/0002698 A1 | 1/2020 | Corgie et al. |
| 2020/0061597 A1 | 2/2020 | Corgie et al. |
| 2020/0330967 A1 | 10/2020 | Corgi |

FOREIGN PATENT DOCUMENTS

| | | |
|---|---|---|
| CN | 101198255 A | 6/2008 |
| CN | 102329008 A | 1/2012 |
| CN | 102329008 B | 1/2013 |
| CN | 103675115 A | 3/2014 |
| CN | 104624166 A | 5/2015 |
| CN | 104624166 B | 6/2017 |
| EP | 1028628 A1 | 8/2000 |
| EP | 1028628 B1 | 2/2003 |
| EP | 2110175 A1 | 10/2009 |
| EP | 2593544 A2 | 5/2013 |
| EP | 1476753 B1 | 8/2013 |
| EP | 3159141 A1 | 4/2017 |
| GB | 2211504 A | 7/1989 |
| JP | 2002128618 A | 5/2002 |
| JP | 2005532533 A | 10/2005 |
| JP | 2008543850 A | 12/2008 |
| JP | 4598403 B2 | 12/2010 |
| KR | 2011/033575 A | 3/2011 |
| SU | 1000098 | 2/1983 |
| WO | 8802600 A1 | 4/1988 |
| WO | 9111105 A1 | 8/1991 |
| WO | 95/012392 A1 | 5/1995 |
| WO | 199715664 A1 | 5/1997 |
| WO | 9922597 A1 | 5/1999 |
| WO | WO9922597 A1 | 5/1999 |
| WO | WO-0031273 A2 | 6/2000 |
| WO | 2003084982 A2 | 10/2003 |
| WO | WO03080796 A2 | 10/2003 |
| WO | WO2006004557 A1 | 1/2006 |
| WO | 2006138271 A1 | 12/2006 |
| WO | 2008156948 A2 | 12/2008 |
| WO | WO2009115335 A1 | 9/2009 |
| WO | 2011161261 A1 | 12/2011 |
| WO | 2012010295 A1 | 1/2012 |
| WO | 2012023847 A2 | 2/2012 |
| WO | 2012122437 A2 | 9/2012 |
| WO | WO2012122437 A2 | 9/2012 |
| WO | WO2012122437 A3 | 9/2012 |
| WO | 2013046165 A1 | 4/2013 |
| WO | WO2013109057 A1 | 7/2013 |
| WO | 2013170050 A1 | 11/2013 |
| WO | 2014055853 A1 | 4/2014 |
| WO | WO-2014055853 A1 * | 4/2014 ............... A62D 3/02 |
| WO | 2014083048 A1 | 6/2014 |
| WO | WO2015078241 A1 | 6/2015 |
| WO | 2015100432 A2 | 7/2015 |
| WO | WO2015111030 A2 | 7/2015 |
| WO | WO2015113047 A2 | 7/2015 |
| WO | WO2015145222 A2 | 10/2015 |
| WO | WO2015157530 A2 | 10/2015 |
| WO | 2016138477 A1 | 9/2016 |
| WO | 2016186879 A1 | 11/2016 |
| WO | 2017011292 A1 | 1/2017 |
| WO | 2017180383 A1 | 10/2017 |
| WO | 2018034877 A1 | 2/2018 |
| WO | 2018102319 A1 | 6/2018 |
| WO | 2020051159 A1 | 3/2020 |
| WO | 2020069227 A1 | 4/2020 |

OTHER PUBLICATIONS

Davis, M. et al., "Formation of Three-Dimensional Ordered Hierarchically Porous Metal Oxides Vi Hybridized Epoxide Assisted/Colloidal Templating Approach", ACS Applied Materials & Interfaces 5:7786-7792 (2013).

Niu T. et al., "Preparation of Meso-Macroporous alpha-Alumina Using Carbon Nanotube as the Template for the Mesopore and Their Application to the Preferential Oxidation of CO in H2-Rich Gases", J Porous Mater 20:789-798 (2013).

Seelan S. et al., "Macroporous Ceramics Coated With Mesoporous Layer for Enzyme Encapsulation", Key Engineering Materials 317-318: 717-722 (2006).

Veitch N.C., "Horseradish Peroxidase: A Modern View of a Classic Enzyme", Phytochemistry 65:249-259 (2004).

Yang L. et al., "Robust Macroporous Materials of Chiral Polyaniline Composites", Chem. Mater. 18(2): 297-300 (2006).

Kim, M. et al., Colorimetric Quantification of Galactose Using a Nanostructured Multicatalyst System . . . Analyst 137(5)1137-1143, 2012.

Lee J. et al., Magnetically Separable and Highly Stable Enzyme System Based on Crosslinked Enzyme Aggregates Shipped in Magnetite Coated Mesoporous Silica J of Materials Chemistry 19(42)864-70, 2009.

Wang Hongying et al. Study on Immobilization of α-Amylase on Magnetic Polyvinyl Alcohol Microspheres,Science and Technology of Food Industry , vol. 28, No. 3, (2007). English Abstract only.

Ahmad et al., Physico-Chemical Processes. Water Environment Research, vol. 77, No. 6, Literature Reviews [CD-ROM content}, pp. 982-1156 (2005).

Adams et al. Specificity of Glucose Oxidase. Archives of Biochemistry and Biophysics 91 (1960) 230-234.

Ansari et al. Potential applications of enzymes immobilized on/in nano materials: A review. Biotechnology Advances 30 (2012) 512-523.

Anthon et al. Colorimetric Method for the Determination of Lipoxygenase Activity. J. Agric. Food Chem. 49 (2001) 32-37.

Banerjee et al. A High-Throughput Colorimetric Assay for Enantioselective Screening of Nitrilase-Producing Microorganisms Using pH Sensitive Indicators. Journal of Biomolecular Screening 8(5); 2003, pp. 559-565.

Baskar et al., Magnetic immobilization and characterization of beta-amylase as nanobiocatalyst for hydrolysis of sweet potato starch. Biochemical Engineering Journal 102 (2015) 18-23.

Cassimjee. ω-Transaminase in Biocatalysis Methods, ractions and Engineering. Doctoral Thesis KTH Royal Institute of Technology, School of Biotechnology Stockholm (2012).

(56) References Cited

OTHER PUBLICATIONS

Dong et al. Efficient biosynthesis of uridine diphosphate glucose from maltodextrin by multiple enzymes immoblized on magnetic nanoparticles. Carbohydrate Research 345, (2010) 1622-1626.
Errede et al. Oxidation of ferrocytochrome c by mitochondrial cytochrome c oxidase. Proc. Nat. Acad. Sci. USA, vol. 73, No. 1, pp. 113-117, Jan. 1976.
Gebreyohannes et al. Nanoscale tuning of enzyme localization for enhanced reactor performance in a novel magnetic-responsive biocatalytic membrane reactor. Journal of Membrane Science 487 (2015) 209-220.
Illanes et al. Recent trends in biocatalysis engineering. Bioresource Technology 115 (2012) 48-57.
Kam et al. Nanotechnology and in Situ Remediation: A Review of the Benefits and Potential Risks. Environmental Health Perspectives, vol. 117, No. 12 (Dec. 2009), pp. 1823-1831.
Khan et al. Hazardous Waste Treatment Technologies. Water Environment Research, vol. 79, No. 10, Literature Reviews [CD-ROM content] (2007), pp. 1858-1902.
Kim et al. Hazardous Waste Treatment Technologies. Water Environment Research, vol. 64, No. 4, 1992: Literature Review (Jun. 1992), pp. 469-479.
Kim et al. Single enzyme nanoparticles in nanoporous silica: A hierarchical approach to enzyme stabilization and immobilization. Enzyme and Microbial Technology 39 (2006) 272-480.
Kim et al. Nanobiocatalysis and its potential applications. Trends in Biotechnology vol. 26, No. 11 (2008) 639-646.
Neto. Process Considerations for the Asymmetric Synthesis of Chiral Amines using w-Transaminase. Thesis, center for Process Engineering and Technology Department of Chemical and Biochemical Engineering Technical University of Denmark, Aug. 2013, pp. 1-108 and 109-117.
Rai et al. Optimization for production of liquid nitrogen fertilizer from the degradation of chicken feather by iron-oxide (Fe3O4) magnetic nanoparticles couples β-keratinase. Biocatalysis and Agricultural Biotechnology, vol. 4, Issue 4, Oct. 2015, pp. 1-13.
Sanders et al., Self-Assembly Using Dynamic Combinatorial Chemistry. Philosophical Transactions: Mathematical, Physical and Engineering Sciences, vol. 362, No. 1819, Organizing Atoms: Manipulation of Matter on the Sub-10 nm Scale (Jun. 15, 2004) pp. 1239-1245.
Sheldon et al. Enzyme immobilisation in biocatalysis: why, what and how. Chem. Soc. Rev. 2013, vol. 42, 6223-6225.
Tappel et al. E. Lipoxidase. H. F. Linskens et al. (eds.) Modern Methods of Plant Analysis/Moderne Methoden der Pflanzenanalyse Springer-Verlag OHG. Berlin—Goettingen—Heidelberg 1964—pp. 469-471.
Tundo et al. methods and Reagents for Green Chemistry: An Introduction. 2007. A John Wiley & Sons Inc. Publication, pp. 1-312 (333 pages total).
Villaverde et al. Hydroperoxide production from linoleic acid by heterologous Gaeumannomyces graminis tritici poxygenase: Optimization and scale-up. Chemical Engineering Journal 214 (2013) 82-90.
Villaverde et al. Analysis of linoleic acid hydroperoxides generated by biomimetic and enzymatic systems through an integrated methodology. Industrial Crops and Products 34 (2011) 1474-1481.
Wang et al. Enhanced phenol degradation in coking wastewater by immobilized laccase on magnetic mesoporous silica nanoparticles in a magnetically stabilized fluidized bed. Bioresource Technology 110 (2012) 120-124.
Wilson et al. Glucose oxidase: an ideal enzyme. Biosensors and Bioelectronics 7 (1992) 165-185.
Zheng et al. Effect of molecular mobility on coupled enzymatic reactions involving cofactor regeneration using nanoparticle-attached enzymes Journal of Biotechnology 154 (2011) 274-280.
The Journal Record News Briefs: Feb. 15, 2010, The Journal Record (Oklahoma City, OK) Feb. 15, 2010 Monday, pp. 1-5.
Three better ways to upcycle waste oil; NUS researchers offer cheaper, greener methods to produce biodiesel The Straits Times (Singapore), Apr. 18, 2015 Saturday, pp. 1-2.
English abstract only of International Application No. WO 03/084982.
Chinese Office Action dated Apr. 28, 2015 received from Application No. 201280022702.9, together with an language translation.
Azevedo A.M. et al., "Horseradish Peroxidase: A Valuable Tool in Biotechnology", Biotechnology Annual Review 9:199-247 (2003).
Chalkias N.G. et al., "Activity Increase of Horseradish Peroxidase in the Presence of Magnetic Particles", J. Am. Chem. Soc. 130:2910-2911 (2008).
Corgie S.C. et al., Self-Assembled Complexes of Horseradish Peroxidase with Magnetic Nanoparticles Showing Enhanced Peroxidase Activity, Advanced Functional Materials 22:1940-1951 (Feb. 15, 2012).
Corvini P.F.X. et al., "LANCE: Laccase-Nanoparticle Conjugates for the Elimination of Micropollutants (Endocrine Disrupting Chemicals) from Wastewater in Bioreactors", Rev Environ Sci Biotechnol 9:23-27 (2010).
Huang J. et al., "Zinc Tetraaminophthalocyanine-Fe3O4 Nanoparticle Composite for Laccase Immobilization", International Journal of Nanomedicine 2(4): 775-784 (2007).
Luo X-L et al., "Electrochemically Deposited Chitosan Hydrogel for Horseradish Peroxidase Immobilization Through Gold Nanoparticles Self-Assembly", Biosensors and Bioelectronics 21:190-196 (2005).
Tang D. et al., "Direct Electrochemical Immunoassay Based on Immobilization of Protein-Magnetic Nanoparticle Composites on to Magnetic Electrode Surfaces by Sterically Enhanced Magnetic Field Force", Biotechnology Letters 28:559-565 (2006).
Wang F. et al., "Magnetic Mesoporous Silica Nanoparticles: Fabrication and Their Laccase Immobilization Perforamnce", Bioresource Technology 101:8931-8935 (2010).
Yang H-H et al., "Magnetite-Containing Spherical Silica Nanoparticles for Biocatalysis and Bioseparations", Analytical Chemistry 76(5): 1316-1321 (Mar. 1, 2004).
International Search Report dated Oct. 10, 2012 received from the Korean Intellectual Property Office from related Application No. PCT/US2012/028392.
International Search Report dated Feb. 20, 2014 received from the Russian Patent Office from related Application No. PCT/US2013/063441.
Morrison et al. Peroxidase-catalyzed halogenation. Annual Review of Biochemistry, vol. 45, 861-888, 1976.
Abril et al. "Enzymatic Baeyer-Villiger Type Oxidations of Ketones Catalyzed by Cyclohexanone Oxygenase," Bioorg. Chem., vol. 17, pp. 41-52 (1989).
Di Nardo et al. "Optimization of the Bacterial Cytochrome P450 BM3 System for the Production of Human Drug Metabolites," Int. J. Mol. Sci., vol. 13, pp. 15901-15924 (2012).
Aguila, Sergio et al. "Stereoselective oxidation of R-(+)-limonene by chloroperoxidase from Caldariomyces fumago," Green Chemistry 10(52):647-653 (2008).
Altschul, Stephen F. et al. "Basic Local Alignment Search Tool," J. Mol. Biol. 215:403-410 (1990).
Banerjee, Anirban et al. "A rapid and sensitive fluorometric assay method for the determination of nitrilase activity," Biotechnol. Appl. Biochem. 37(3):289-293 (2003).
Betancor, Lorena et al. "Preparation of a Stable Biocatalyst of Bovine Liver Catalase Using Immobilization and Postimmobilization Techniques," Biotechnology Progress 19(3):763-767 (2003).
Chau, Yat-Pang et al. "Differential permeability of blood microvasculatures in various sympathetic ganglia of rodents," Anatomy and Embryology, 194(3):259-269 (1996).
Corgie, Stephane et al. "Universal enzyme immobilisation within hierarchically-assembled magnetic scaffolds," Chem. Today 34(5):15-20 (2016).
Dadashipour, Mohammad et al. "Hydroxynitrile Lyases: Insights into Biochemistry, Discovery, and Engineering," ACS Catal. 1:1121-49 (2011).
Denisov, Llia et al. "Structure and Chemistry of Cytochrome P450," Chem. Rev. 105(6):2253-77 (2005).

(56) References Cited

OTHER PUBLICATIONS

Dresser, George K. et al. "Pharmacokinetic-Pharmacodynamic Consequences and Clinical Relevance of Cytochrome P450 3A4 Inhibition," Clinical Pharmacokinetics 38(1):41-57 (2012).
Duan, Xiaonan et al. "Hierarchical Hybrid Peroxidase Catalysts for Remediation of Phenol Wastewater," ChemPhysChem, 15(5):974-980 (2014).
Fiers, W. et al., "Complete nucleotide sequence of SV40 DNA," Nature 273: 113-120 (1978).
Glieder, Anton et al. "Comprehensive Step-by-Step Engineering of an (R)-Hydroxynitrile Lyase for Large-Scale Asymmetric Synthesis**," Angew. Chem. Int. Ed. 42:4815 (2003).
Greenaway, P.J. et al. "Human cytomegalovirus DNA: BumHI, EcoRI and Pst I restriction endonuclease cleavage maps," Gene 18: 355-360 (1982).
Gupta, Namita et al. "Simplified para-nitrophenyl palmitate assay for lipases and esterases," Analytical Biochemistry 311:98-99 (2002).
Hess, B. et al. "Cooperation of Glycolytic Enzymes," J. Adv. Enzyme Res. 7:149 (1968).
Hitzeman, Ronald A. et al., "Isolation and Characterization of the Yeast 3-Phosphoglycerokinase Gene (PGK) by an Immunological Screening Technique*," J. Biol. Chem. 255:2073 (1980).
Holland, Michael J. et al., "Isolation and Identification of Yeast Messenger Ribonucleic Acids Coding for Enolase, Glyceraldehyde-3-phosphate Dehydrogenase, and Phosphoglycerate Kinase," Biochemistry 17:4900 (1978).
Ribarne, Christelle et al. "Involvement of Cytochrome P450 3A4 Enzyme in the N-Demethylation of Methadone in Human Liver Microsomes," Chem. Res. Tox. 9(2): p. 365-373 (1996).
Jones, G.M. et al. "Environmental *Streptococcal* and Coliform Mastitis," Virgina Cooperative Extension, Publ. 404-234, 2009.
Jones, G.M. "Understanding the Basics of Mastitis," Virgina Cooperative Extension, Publ. 404-233, 2009.
Joo, Hyun et al. "Laboratory evolution of peroxide-mediated cytochrome P450 hydroxylation," Nature, 399 (6737):670-673 (1999).
Kim, H. et al. "Cytochrome P450 isozymes responsible for the metabolism of toluene and styrene in human liver microsomes," Xenobiotica 27(7):657-665 (1997).
Kusumoto, I. "Industrial Production of L-Glutamine," American Society for Nutritional Sciences, 131:2552S-2555S (2001).
Lindskog et al. The catalytic mechanism of mammalian carbonic anhydrases New Horizons 7:175-95 (2000).
Lucas, John A. et al. "The Evolution of Fungicide Resistance," Advances in Applied Microbiology, vol. 90, 2015.
Mathew, Sam et al. "ω-Transaminases for the Production of Optically Pure Amines and Unnatural Amino Acids," ACS Catalysis 2(6):993-1001 (2012).
Moses, Marion. "Pesticide-Related Health Problems and Farmworkers," AAOHN J., 37(3):115-30 (1989).
Needleman, Saul B. et al. "A General Method Applicable to the Search for Similarities in the Amino Acid Sequence of Two Proteins," J. Mol. Biol. 48:443 (1970).
Pearson, William R. et al. "Improved tools for biological sequence comparison," Proc. Natl. Acad. Sci. vol. 85, pp. 2444-2448, Apr. 1988.
Ritter, L. et al. "Addressing the Linkage between Exposure to Pesticides and Human Health Effects—Research Trends and Priorities for Research," J Tox. Environ. Health 9(6):441-56 (2006).
Sawayama, Andrew M. et al. "A Panel of Cytochrome P450 BM3 Variants To Produce Drug Metabolites and Diversify Lead Compounds," Chemistry 15(43):11723-9 (2009).
Schätzle, Sebastian et al. "Rapid and Sensitive Kinetic Assay for Characterization of ω-Transaminases," Analytical Chemistry 81(19):8244-8248 (2009).
Shaw, Nicholas M. et al. "Lonza: 20 Years of Biotransformations," Adv. Synth. and Catalysis 345(4): 425-435 (2003).
Shingles, Richard et al. "Direct Measurement of ATP-Dependent Proton Concentration Changes and Characterization of a K+-Stimulated ATPase in Pea Chloroplast Inner Envelope Vesicles," Plant Physiol. 106(2):731-737 (1994).
Shingles, Richard et al. "Measurement of Carbonic Anhydrase Activity Using a Sensitive Fluorometric Assay," Analytical Biochemistry 252(1):190-197 (1997).
Sorouraddin, M.H. et al. "Spectrophotometric determination of some catecholamine drugs using sodium bismutha," Journal of Pharmaceutical and Biomedical Analysis 18:877-881 (1998).
Tsotsou, Georgia E. et al. "High throughput assay for cytochrome P450 BM3 for screening libraries of substrates and combinatorial mutants," Biosensors & Bioelectronics, 17:119-131 (2002).
Wan, Feng-Yi et al. "The influence of oxidation of membrane thiol groups on lysosomal proton permeability," Biochemistry Journal, 360, 355-362 (2001).
Welk, A. et al. "Microbicidal efficacy of thiocyanate hydrogen peroxide after adding lactoperoxidase under saliva loading in the quantitative suspension test," Archives of Oral Biology, 56:1576-1582 (2011).
Wells, Andrew. "What Is in a Biocatalyst?," Organic Process Res. Dev. 10:678-681 (2006).
Wilbur, Karl M. et al. "Electrometric and Colorimetric Determination of Carbonic Anhydrase," J. Biol. Chem. 176:147-154 (1948).
Wrighton, Steven A. et al. "The Human Hepatic Cytochromes P450 Involved in Drug Metabolism," Crit. Rev. Tox. 22(1):1-21 (1992).
Yamazaki, Hiroshi et al., "Roles of Cytochromes P450 1A2 and 3A4 in the Oxidation of Estradiol and Estrone in Human Liver Microsomes," Chem. Res. Tox. 11(6): p. 659-665 (1998).
U.S. Appl. No. 62/163,032, filed May 18, 2015.
U.S. Appl. No. 62/193,041, filed Jul. 15, 2015.
U.S. Appl. No. 62/323,663, filed Apr. 16, 2016.
Bhosale, S. et al., "Molecular and Industrial Aspects of Glucose Isomerase," Microbiol. Rev. 60(2):280-300 (1996).
Bosch, E.H. et al.,"The lactoperoxidase system: the influence of iodide and the chemical and antimicrobial stability over the period of about 18 months," J. Applied Microbiol., 89(2), 215-24 (2000).
Alexander et al. "Cytochrome P450 (E.C. 1.14.-.-)bph_506_108a 215," Br. J. Pharmacol. 158(Suppl 1): S215-S217 (2009).
Bradford, Marion M. "A Rapid and Sensitive Method for the Quantitation of Microgram Quantities of Protein Utilizing the Principle of Protein-Dye Binding," Analytical Biochemistry, 72(1-2):248-254 (1976).
Boone, Christopher D. et al. "Carbonic Anhydrase: An Efficient Enzyme with Possible Global Implications," International Journal of Chemical Engineering, vol. 2013, Article ID 813931, 2013.
Caswell, Jill M. et al. "From P450 Discovery To Scale-Up for Delivery of Chiral Intermediates," Department of Biocatalysisand Isotope Chemistry, Almac Sciences, UK, downloaded from https://www.almacgroup.com in 2015.
Duong, The-Phong et al. "Characterization of Mechanical Properties of Magnetite-polymer Composite Films," Proceedings of the XIth International Congress and Exposition, Jun. 2-5, 2008 Orlando, Florida USA.
Hoffmann, Sandra et al. "Annual Cost of Illness and Quality-Adjusted Life Year Losses in the United States Due to 14 Foodborne Pathogens," Journal of Food Protection, vol. 75, No. 7, pp. 1292-1302, 2012.
Kim, J. et al. A magnetically separable, highly stable enzyme system based on nanocomposites of enzymes and magnetic nanoparticles shipped in hierarchically ordered, mesocellular, mesoporous silica. Small. 2005. vol. 1. No. 12. pp. 1203-1207.
Kirkman, Henry N. et al. "Catalase: A tetrameric enzyme with four tightly bound molecules of NADPH," Proc. Natl. Acad. Sci USA, vol. 81, pp. 4343-4347, Jul. 1984.
McCall, Keith A. et al. "Function and Mechanism of Zinc Metalloenzymes," American Society for Nutritional Sciences, 1437S-1446S, 2000.
Mix, Stefan. "Shortening the Path—Pharmaceutical Materials from Enzymatic Reactions," Almac Group, Organic Process Research & Development Prague, Oct. 17-19, 2016.
PCT International Preliminary Report on Patentability dated Jul. 31, 2017 for PCT/US2016/041461 filed on Jul. 8, 2016, 10 pages.
PCT International Preliminary Report on Patentability dated Nov. 21, 2017 for PCT/US2016/031419 filed on May 9, 2016, 8 pages.
PCT Search Report and Written Opinion dated Jul. 27, 2016 for PCT/US2016/031419 filed on May 9, 2016, 16 pages.

(56) References Cited

OTHER PUBLICATIONS

PCT Search Report and Written Opinion dated Jul. 3, 2017 for PCT/US2017/026086 filed on Apr. 5, 2017, 22 pages.
PCT Search Report and Written Opinion dated Oct. 25, 2017 for PCT/US2017/045655 filed on Aug. 6, 2017, 12 pages.
PCT Search Report and Written Opinion dated Sep. 16, 2016 for PCT/US2016/041461 filed on Jul. 8, 2016, 11 pages.
Porter, Michael M. et al. "Biomimetic Materials by Freeze Casting," JOM: the journal of the Minerals, Metals, and Materials Society, 65(6), Apr. 2013.
Sawayama, Andrew M. et al. "A Panel of Cytochrome P450 BM3 Variants to Produce Drug Metabolites and Diversify Lead Compounds," Chem. Eur. J. 2009.
Wainaina, James et al. "Synthesis of Magnetite/Amphiphilic Polymer Composite Nanoparticles as Potential Theragnostic Agents," Journal of Nanoscience and Nanotechnology, vol. 12, 5920-5924, 2012.
Yamagata, Mika et al. "Magnetite/Polymer Composite Particles Prepared by Molecular Assembling Followed by In-Situ Magnetite Formation," Macromol. Symp., 245-246, 363-370, 2006.
PCT Search Report and Written Opinion dated Feb. 12, 2018 for PCT/US2017/063542 filed on Nov. 28, 2017, 9 pages.
El-Zahab et al. "Enabling multienzyme biocatalysis using nanoporous materials," Biotechnol Bioeng, vol. 87, No. 2, pp. 178-183, Jul. 20, 2004.
Liu et al. "Nanoparticle-supported multi-enzyme biocatalysis with in situ cofactor regeneration," J Biotechnol, vol. 139, No. 1, pp. 102-107, Oct. 19, 2008.
Petkova et al. "Synthesis of silica particles and their application as supports for alcohol dehydrogenases and cofactor immobilizations: conformational changes that lead to switch in enzyme stereoselectivity," Biochim Biophys Acta, vol. 1824, No. 6, pp. 792-801, Mar. 26, 2012.
Zheng et al. "Magnetic field intensified bi-enzyme system with in situ cofactor regeneration supported by magnetic nanoparticles," J Biotechnol, vol. 168, No. 2, pp. 212-217, Jun. 10, 2013.
Carozza, Susan E. et al. "Risk of Childhood Cancers Associated with Residence in Agriculturally Intense Areas in the United States," Environ. Health Perspect. 116(4):559-65 (2008).
Corning, Website at https://www.corning.com/worldwide/en/products/life-sciences/products/adme-tox-research/recombinant-metabolic-enzymes.html. Downloaded Mar. 4, 2018.
CYPEX, Website located at http://www.cypex.co.uk/ ezcypbuf.htm. Dowloaded on Mar. 4, 2018.
Cytochrome c Oxidase Assay Kit, Sigma-Aldrich 2014:1-4; website located at https://www.ncbi.nlm.nih.gov/pmc/articles/PMC2884625/. Downloaded on Mar. 4, 2018.
Gong, Jin-Song et al., "Nitrilases in nitrile biocatalysis: recent progress and forthcoming research," Microbial Cell Factories 11(1):142 (2012).
Kerr, Susan. "Drying-Off Lactating Livestock," Small Farms vol. V, No. 3 (2010).
Kirkman, Henry N. et al. "Catalase: A tetrameric enzyme with four tightly bound molecules of NADPH," Proc. Natl. Acad. Sci. USA. 81(14):4343-7 (1984).
Li, Yi et al. "Rapid Kinetic Microassay for Catalase Activity," J. Biomolecular Techniques 18(4):185-187 (2007).
Mark, Genevieve L. et al. "Molecular-based strategies to exploitPseudomonas biocontrol strains forenvironmental biotechnologyapplications," FEMS Microbiol Ecol. 56(2):167-77 (2006).
Newsholme, Philip et al. "Glutamine and glutamate—their central role in cell metabolism and function," Cell Biochem. and Function, 21:1-9 (2003).
Nielsen, Christel. "Economic Impact of Mastitis in Dairy Cows," Department of Animal Breeding and Genetics, Uppsala, Sweden, Swedish University of Agricultural Sciences (2009).
Purdy, Michael A. et al. "Effect of Growth Phase and Cell Envelope Structure on Susceptibility of *Salmonella typhimurium* to the Lactoperoxidase-Thiocyanate-Hydrogen Peroxide System," Infection and Immunity, 39(3), 1187-1195 (1983).
Reeves, Margaret et al. "Greater Risks, Fewer Rights: U.S. Farmworkers and Pesticides," Int'l J., Occup. Environ. Health 9(1):30-39 (2003).
Reiter, Bruno et al. "Nonspecific Bactericidal Activity of the Lactoperoxidase-Thiocyanate-Hydrogen Peroxide System of Milk Against *Escherichia coli* and Some Gram-Negative Pathogens," Infection and Immunity, 13(3), 800-307 (1976).
Sigma Chemical Corporation and Kessey, J. (1994) Enzymatic Assay of Choline Oxidase (EC 1.1.3.17). https://www.sigmaaldrich.com/content/dam/sigma-aldrich/docs/Sigma/Enzyme_Assay/c5896enz.pdf.
Smith, Temple F. et al. "Comparison of Biosequences," Adv. Appl. Math. 2:482-489 (1981).
Tang, Cuyue et al. "Major Role of Human Liver Microsomal Cytochrome P450 2C9 (CYP2C9) in the Oxidative Metabolism of Celecoxib, a Novel Cyclooxygenase-II Inhibitor," J. Pharm. Exp. Therap., 293(2):453-459 (2000).
Trefzer, Axel et al. "Biocatalytic Conversion of Avermectin to 4'-Oxo-Avermectin: Improvement of Cytochrome P450 Monooxygenase Specificity by Directed Evolution," Appl Environ. Microbiol. 73(13):4317-4325 (2007).
Xia, Menghang et al. "Compound Cytotoxicity Profiling Using Quantitative High-Throughput Screening," Environmental Health Perspectives, 116(3):284-291 (2008).
Zhu, Mingshe et al. "Cytochrome P450 3A-Mediated Metabolism of Buspirone in Human Liver Microsomes," Drug Metabolism and Disposition 33(4):500-507 (2005).
World Health Day, Combat Drug Resistance: No Action Today Means No Cure Tomorrow, Statement by WHO Director-General, Dr. Margaret Chan, Apr. 6, 2011, http://www.who.int/mediacentre/news/statements/2011/whd_20110407/en/. Downloaded Mar. 4, 2018.
Antibiotic Resistance Threats in the United States, 2013, Centers for Disease Control and Prevention: Atlanta, GA, http://www.cdc.gov/drugresistance/threat-report-2013/. Downloaded Mar. 4, 2018.
Roberts, Rebecca R. et al. "Hospital and Societal Costs of Antimicrobial-Resistant Infections in a Chicago Teaching Hospital: Implications for Antibiotic Stewardship," Clin. Infect. Dis. 49(8):1175-84 (2009).
Hoffmann, S. et al. Making Sense of Recent Cost-of-Foodborne-Illness Estimates, United States Department of Agriculture, Economic Research Service, 2013, http://www.ers.usda.gov/publications/eib-economic-information-bulletin/eib118.aspx. Downloaded Mar. 4, 2018.
U.S. Department of Health and Human Services Food and Drug Administration Center for Drug Evaluation and Research (CDER)"Safety Testing of Drug Metabolites Guidance for Industry", Nov. 2016.
"Agriculture," Merriam-Webster, <https://www.merriam-webster.com/dictionary/agriculture>, published Jun. 5, 2012, p. 1.
Corgie et al. "Self-Assemblies of Magnetic Nanoparticles (MNPs) and Peroxidase Enzymes: Mesoporous Structures and Nanoscale Magnetic Field Effects (nano-MFEs) for Enhanced Activity BioNanoCatalysts (BNCs)"; Cleantech, www.ct-si.org; Dec. 2012.
Hielscher, Thomas. "Ultrasonic production of nano-size dispersions and emulsions," ENS 05, Paris, France, XP-002788816, Dec. 2005.
Lee et al. "Microfluidic continuous magnetophoretic protein separation using nanoparticle aggregates," Microfluidics and Nanofluidics, Springer, Berlin, DE, vol. 11, No. 4, May 2011.
Demirel, D. et al. Preparation and characterization of magnetic duolite-polystyrene composite particles for enzyme immobilization, Journal of Food Engineering, 62(2004)203-208.
European Search Report for European application No. 17782855.5 dated Nov. 11, 2019.
PCT Search Report and Written Opinion dated Dec. 23, 2019 for PCT/US19/49397.
PCT Search Report and Written Opinion dated Dec. 11, 2019 for PCT/US19/53307.
Zheng, M. et al. "Magnetic field intensified bi-enzyme system with in situ cofactor regeneration . . . "Journal of Biotechnology vol. 168 No. 2 (Oct. 2013).

(56) References Cited

OTHER PUBLICATIONS

Pecova, M. et al. "Thermostable trypsin conjugates immobilized to biogenic magnetite show a high operational stability and remarkable reusability for protein digestion," Nanotechnology 2013 vol. 2013 125102 pp. 1-11.
Hydrolase Nomenclature excerpt from Enzyme Nomenclature Recommendations Nomenclature Committee of the International Union of Biochemistry and Molecular Biology download from https://www.qmul.ac.uk/sbcs/iubmb/enzyme/EC3/ on Nov. 22, 2019.
MeSH Lactoperoxidase information downloaded Oct. 1, 2018 at https:/lwww.ncbi.nlm.nih.gov/mesh/?term=lactoperoxidase.
Merriam-Webster, "Matrix", <https://www.merriam-webster.com/dictionary/matrix>. Copyright 2020 Merriam-Webster, Incorporated.
PCT Search Report and Written Opinion dated Jun. 13, 2022, for PCT/US2021/061493.
Bhattacharjee et al."Nanofibrous Nonmulberry Silk/PVA Scaffold for Osteoinduction and Osseointegration", Biopolymers, 2015, vol. 103, No. 5, pp. 271-284.

\* cited by examiner

Plate layout

*Pseudomonas syringae 14045-8b*

Non-coated tomato seeds | Coated tomato seeds

*Clavibacter michiganensis 0690*

Non-coated tomato seeds   Coated tomato seeds

MAGNETICALLY IMMOBILIZED MICROBIOCIDAL ENZYMES

CROSS REFERENCE TO RELATED APPLICATIONS

This application is a divisional of U.S. application Ser. No. 15/572,306 filed Nov. 7, 2017, which is a National Phase Application of PCT/US2016/031419 filed May 9, 2016 and claims the benefit of U.S. Provisional Application No. 62/163,032, filed on May 18, 2015 and U.S. Provisional Application No. 62/215,713, filed on Sep. 8, 2015. All are incorporated herein by reference in their entirety.

FIELD OF THE INVENTION

The present invention provides compositions and methods for reducing microbial contamination or infection in plants, animals, fabrics, and products therefrom. The present invention also provides compositions and methods for reducing human infections. In particular, it provides solid magnetic nanoparticles comprising bacteriostatic, bacteriocidal, fungistatic, and fungicidal enzymes in one component, and substrates for the enzymes in another component. The compositions are dormant and become active upon exposure to hydration and oxygen.

BACKGROUND OF THE INVENTION

Contaminating and infectious microorganisms significantly reduce the yield, quality, and safety of agricultural and animal products worldwide. The resulting economic losses are in the tens of billions of dollars annually in the United States alone. In addition, current methods for reducing animal infections rely on the harmful overuse of antibiotics that stay in the food chain and result in multidrug resistant "superbugs." These bacteria have been selected to survive in the presence of medically important antibiotics and are a significant threat to human health.

Seeds can spread plant diseases across farms, states, and countries. Control of such diseases may begin with the seeds. Seed treatments should protect seeds from pathogens such as bacteria, viruses, and fungi. Thus, high-quality, disease-free seeds are an important part of obtaining higher plant yields and food safety.

For example, Tomato production in the United States are severely threatened by bacterial leaf spot (BLS), a disease caused by *Xanthomonas* spp. It is a devastating disease resulting in tremendous economic losses with reports that the pathogen causes as much as $87 million of losses for the fresh tomato sector each year in Florida alone. BLS is caused by four main species of *Xanthomonas: X euvesicartoria, X perforans* (i.e., *X. axonopodis* pv. *vesicatoria*), *X. vesicatoria* and *X. gardneri*, and exotic strains have been recently been introduced.

The bacterial infection produces individual spots (lesions) on leaves and fruit that decrease crop yields. Bacterial cell invasion of host tissues cause the entire plant to wilt and dramatically decreases the plants' ability to photosynthesize and produce fruit. Fruit spots do not penetrate very deeply into the tomato fruits but they do lower the value of fresh tomatoes because consumers generally do not want to eat fruits and vegetables that are covered in raised, scabby black spots. Furthermore, there are a variety of fungi and other bacteria that can colonize the lesions that establish secondary infections and cause fruit rot. While *Xanthomonas* spp. can cause minor cases of BLS on mature fruit, the majority of crop loss is caused by early infections, which leads to the shedding of blossoms and dropping of young fruit.

Plant pathogens are often disseminated by the transmission of propagation material, including seeds, transplants, bulbs and other propagation material. Seed contamination is a main cause of *Xanthomonas* spp.-caused BLS outbreaks although volunteer host plants are another source of infection. It has been shown that *Xanthomonas* can survive on and within seeds for more than 16.5 months, and possibly even many years. The cotyledons, or embryonic leaves, become infected when they emerge from a seed with a contaminated seedcoat. Even if only a few seeds are contaminated, they can devastate a field because infected seedlings will infect neighboring seedlings, which are more susceptible to infection than are mature plants.

Controlling plant pathogens relies heavily on synthetic chemicals such as copper salts to maintain high yields. The public has shown increasing concern, however, for the effects that agrochemical residues have on human health and the environment (Mark et al., *FEMS Microbiol. Ecol.* 56(2): 167-77 (2006); Ritter et al., *J. Tox. Environ. Health* 9(6): 441-56 (2006)). Studies have shown that farmers who use synthetic agrochemicals have more neurological problems that include headaches, fatigue, insomnia, dizziness and hand tremors (http://www.niehs.nih.gov/health/topics/agents/pesticides/). Agrochemicals may also cause birth defects, nerve damage, cancer, decreased sperm motility and acute poisoning (Moses, *AAOHN J.,* 37(3):115-30 (1989); Reeves and Schafer Int'l J., *Occup. Environ. Health* 9(1): 30-39 (2003); Carozza et al., *Environ. Health Perspect.* 116(4):559-65 (2008); U.S. Environmental Protection Agency, 2014, http://www.epa.gov/pesticides/food/risks.htm).

Bacterial plant pathogens are also controlled with antibiotics. Synthetic bacteriocides, in particular, are of critical concern on crops consumed by humans. The generation of antibiotic-resistant bacteria resulting from their continuous application to crops provides a reservoir of antibiotic-resistant bacteria that can then cause life-threatening human infections.

Thus, there is a tremendous need for safer and effective alternatives for controlling plant pathogens. Furthermore, protecting crops from bacterial pathogens is particularly challenging for organic crops on which synthetic chemicals and antibiotics cannot be used.

Antibiotic resistance in humans and farm animals is developing and spreading at a rate that may not be contained by the development of new drugs. The widespread practice of routinely dosing farm animals with antibiotics is contributing to this threat. Around half of the antibiotics produced globally are used in agriculture. Much of this use promotes faster growth and prevents, rather than treats, disease. Resistant microorganisms carried by farm animals can spread to humans through consumption of contaminated food, from direct contact with animals, or by environmental spread, for example, in contaminated water or soil.

For example, mastitis is an inflammatory reaction of the mammary gland in response to an infection by toxin-releasing bacteria of the teat canal resulting in damaged mammary tissue. This increases vascular permeability and leads to a reduction in milk production and an alteration of milk composition. For example, blood constituents, serum proteins, and enzymes leak into the milk. Also, there is a decrease in caseins, lactose, and fat quality (Harmon, *J. Dairy Sci* 77(7): 2103-2112 (1994); Osteras and Edge *Acta Vet Scand* 41(1): 63-77 (2000); Nielsen, *Economic Impact of*

*Mastitis in Dairy Cows. Department of Animal Breeding and Genetics*, Uppsala, Sweden, Swedish University of Agricultural Sciences. 2009).)

Mastitis is caused by both "contagious" and "environmental pathogens. Contagious pathogens are bacteria that are present only in milk and are spread to uninfected udders during the milking process. Environmental pathogens are present in the environment and infect udders between milkings. In recent years, the epidemiology of mastitis-causing bacteria has changed. The main contagious pathogen, *Streptococcus agalactiae*, has been eradicated from many herds but the other primary contagious pathogen, *Staphylococcus aureus*, has remained prevalent. The most important change, however, is that mastitis caused by environmental pathogens (e.g., *Str. uberis, Str. Dysgalactiae, Enterobacter,* and the coliforms *Escherichia coli* and *Klebsiella* spp.) has risen dramatically (Jones and J. M. Swisher 2009; Jones and T. L. Bailey 2009).

According to the U.S. Department of Agriculture, mastitis is the leading disease that is responsible for the use of antibiotics in U.S. cows. (Kerr, *Drying-Off Lactating Livestock, Small Farms* V (2010).) Given this abundant use of antibiotics, mastitis greatly contributes to increased human health risks.

Likewise, the poultry industry routinely feeds its animals low levels of prophylactic antibiotics that include antibiotics belonging to medically important drug classes. This attempts to avoid diseases and bulks up the birds. This practice, however, selects for drug resistant bacteria that can end up in the human food chain.

Thus, for the reasons described herein, there is a significant need for new methods of controlling microbial infections and contamination in the farm animals.

SUMMARY OF THE INVENTION

The present invention provides compositions and methods for reducing microbial contamination or infection in plants, animals, fabrics, and products therefrom. The present invention also provides compositions and methods for reducing human infections. In particular, it provides solid magnetic nanoparticles comprising stabilized antimicrobial enzymes in one component and substrates for the enzymes in another component. The compositions are dormant and become active upon exposure to hydration and oxygen. Subsequently, the substrates for the enzymes are converted to hydrogen peroxide and free radicals that stop the growth, or kill, microbes and viruses.

The invention provides a new method of agricultural, industrial, and medical microbial control with safe, potent, oxidative agents. The invention is effective against many infectious and spoilage organisms.

Thus, the invention provides solid antimicrobial compositions, comprising; a first component having self-assembled mesoporous aggregates of magnetic nanoparticles comprising a hydrogen peroxide producing enzyme and a free radical producing enzyme; and a second component having a first substrate for said hydrogen peroxide producing enzyme and a second substrate for said free radical producing enzyme; wherein said composition is essentially inactive, wherein exposure of said first and second components to hydration or oxygen activates said composition and results in said substrate for said hydrogen peroxide producing enzyme being oxidized into hydrogen peroxide, wherein said hydrogen peroxide acts as a substrate for said free radical producing enzyme, and wherein said free radicals are produced having microbiostatic or microbiocidal activities.

The invention also provides liquid antimicrobial compositions, comprising; a first component having self-assembled mesoporous aggregates of magnetic nanoparticles comprising a free radical producing enzyme; and a second component having a substrate for said free radical producing enzyme and a hydrogen peroxide source; wherein said composition is essentially inactive, wherein mixing said first and second components activates said composition and results in said hydrogen peroxide source acting as a substrate for said free radical producing enzyme, and wherein said free radicals are produced having microbiostatic or microbiocidal activities.

In some embodiment of the invention, the antimicrobial solid or liquid compositions are bacteriostatic, bacteriocidal, viricidal, or fungicidal.

In some embodiments of the solid antimicrobial composition, said first and second components are layers. In preferred embodiments, one of said layers is internal to the other layer. In more preferred embodiments, the free radical generating enzyme is in said internal layer.

In some embodiments of the solid antimicrobial composition, said first component further comprises a matrix material that is a water-soluble cellulose derivative or water-solvatable cellulose derivative. In other embodiments of the solid antimicrobial composition, said second component further comprises a matrix material that is a water-soluble cellulose derivative or water-solvatable cellulose derivative. In preferred embodiments, said matrix material is carboxymethyl cellulose. In other preferred embodiments, the solid antimicrobial composition further comprises alginate derivatives or chitosan derivatives.

In some embodiments of the invention, said mesoporous aggregates of magnetic nanoparticles have an iron oxide composition. In other embodiments, the mesoporous aggregates of magnetic nanoparticles have a magnetic nanoparticle size distribution in which at least 90% of magnetic nanoparticles have a size of at least 3 nm and up to 30 nm, and an aggregated particle size distribution in which at least 90% of said mesoporous aggregates of magnetic nanoparticles have a size of at least 10 nm and up to 500 nm. In other embodiments, the mesoporous aggregates of magnetic nanoparticles possess a saturated magnetization of at least 10 emu/g.

In some embodiments of the invention, the free-radical-producing enzyme and hydrogen peroxide producing enzyme are contained in mesoporous aggregates of magnetic nanoparticles in up to 100% of saturation capacity.

In some embodiments, the hydrogen peroxide generating enzyme is an oxidase. In preferred embodiments, the oxidase is glucose oxidase or alcohol oxidase. In other embodiments, the substrate for said hydrogen peroxide generating enzyme is ($\beta$-D-Glucose or an alcohol In some embodiments of the invention, the free radical producing enzyme is a peroxidase. In preferred embodiments, the peroxidase is a lactoperoxidase. In other preferred embodiments, the peroxidase is myeloperoxidase, eosinophil peroxidase, or thyroid peroxidase. In other embodiments, the substrate for the peroxidase is thiocyanate, iodide, or bromide. In other preferred embodiments, the free radical generating enzyme produces hypothiocyanite, hypoiodite, or hypobromite.

In some embodiments of the invention, the antimicrobial compositions further comprise a cellulase enzyme. In preferred embodiments, the cellulase enzyme is an exocellulase or an endocellulase. In other preferred embodiments, the cellulase enzyme is incorporated into an outer layer of said antimicrobial composition.

The invention provides agricultural products comprising the antimicrobial compositions described herein. In preferred embodiments, the invention provides liquid pesticides, seed coatings, and improved seeds comprising the antimicrobial compositions described herein.

In more preferred embodiments, the invention provides improved seeds selected from the group consisting of vegetable, fruit, flower and field crops.

In more preferred embodiments, said vegetable seeds are selected from the group consisting of tomato, pea, onion, garlic, parsley, oregano, basil, cilantro, carrot, cabbage, corn, cucumber, radish, pepper, broccoli, cauliflower, cucumber, spinach, kale, chard, artichoke, and lettuce.

In other more preferred embodiments, said fruit seeds are selected from the group consisting of citrus, tomato, orange, lemon, lime, avocado, clementine, apple, persimmon, pear, peach, nectarine, berry, strawberry, raspberry, grape, blueberry, blackberry, cherry, apricot, gourds, squash, zucchini, eggplant, pumpkin, coconut, guava, mango, papaya, melon, honeydew, cantaloupe, watermelon, banana, plantain, pineapple, quince, sorbus, loquata, plum, currant, pomegranate, fig, olive, fruit pit, a nut, peanut, almond, cashew, hazelnut, brazil nut, pistachio, and macadamia. In a most preferred embodiment, said seeds are tomato seeds.

In other more preferred embodiments, said field crops are selected from the group consisting of corn, wheat, soybean, canola, sorghum, potato, sweet potato, yam, lentils, beans, cassava, coffee, hay, buckwheat, oat, barley, rape, switchgrass, elephant grass, beet, sugarcane, and rice.

In other more preferred embodiments, said said flower seeds are selected from the group consisting of annual, perennial, bulb, flowering woody stem, carnation, rose, tulip, poppy, snapdragon, lily, mum, iris, alstroemeria, pom, fuji, and bird of paradise.

The invention provides methods of improving plant product yields comprising exposing the improved seeds described herein to hydration and oxygenation prior to or during the planting or germination of said plants.

The invention provides animal beddings comprising the antimicrobial compositions described herein.

The invention further provides methods of improving animal product yields comprising exposing the animal beddings described herein to hydration and oxygen prior to or during use by said animal. In preferred embodiments, said hydration is from said animal's urine. In preferred embodiments, said animal products may be selected from the group consisting of live animals, milk, meat, fat, eggs, bodily fluids, blood, serum, antibodies, enzymes, rennet, bone, animal byproducts, and animal waste. In other preferred embodiments, said animals may be selected from the group consisting of cows, pigs, chickens, turkeys, horses, sheep, goats, donkeys, mules, ducks, geese, buffalo, camels, yaks, llama, alpacas, mice, rats, dogs, cats, hamsters, guinea pigs, reptiles, amphibians, parrots, parakeets, cockatiels, canaries, pigeons, doves, and insects.

The invention provides wound dressings comprising the antimicrobial compositions described herein. In preferred embodiments, he wound dressings are bandages. In other embodiments, the invention provides methods of reducing sepsis comprising administering the wound dressings described herein to a wound.

The invention provides fabrics comprising the antimicrobial compositions described herein.

The invention provides methods of producing the solid antimicrobial compositions described herein comprising formulating said first component with a matrix material selected from the group consisting of water-soluble cellulose derivatives, water-solvatable cellulose derivatives, alginate derivatives, and chitosan derivatives and formulating said second component with a matrix material selected from the group consisting of water-soluble cellulose derivatives, water-solvatable cellulose derivatives, alginate derivatives, and chitosan derivatives. In preferred embodiments, said first component or said second component is further subjected to spray drying, freeze drying, drum drying, pulse combustion drying, or rotary seed coating.

The invention provides methods of reducing or eliminating microbial pest growth comprising spraying a substance with the liquid antimicrobial compositions disclosed herein.

BRIEF DESCRIPTION OF THE DRAWINGS

FIG. 1. Diagram of a solid antimicrobial assembly and its function when used as a seed coating.

FIG. 2. The velocity of free and immobilized Soy bean peroxidase plus Glucose Oxidase (SB1+GOX-1) is compared using the oxidation of Amplex Red as an indicator. Immobilization increased free radical production efficiency three-fold over free enzymes.

FIGS. 3A and 3B show the efficacy of the LP system against $5\times10^6$ *E. coli* cells in solution after 5 minutes measured by the Live and Dead fluorescent assay. Different concentrations of Glucose or $H_2O_2$ were measured. FIG. 3A: LP/GOX immobilized (hatched) vs. free (solid). FIG. 3B: LP immobilized (hatched) vs. free (solid).

FIGS. 4A and 4B show that SBP and GOX in a solid assembly efficiently killed *Xanthamonas* in vitro. FIG. 4A: BNC-immobilized enzymes were contacted with cellulose film-suspended substrates. FIG. 4B: Upon mixture, hydration, and exposure to a growing bacterial monolayer, the assemblies demonstrated significant growth inhibition after 24 hours.

FIG. 5. Solid assembly coated tomato seed germination after 7 days. No germination inhibition was observed. Test and control seeds showed 85% germination. Germination rate was 100% on wheat assays.

FIG. 6. Schematic diagram of one embodiment where a machine produces improved seeds with the antimicrobial compositions of the invention.

FIG. 7. Diagram of a solid antimicrobial composition and its function when used as an animal bedding coating.

FIG. 8. Schematic diagram of one embodiment where a machine produces improved animal bedding with the antimicrobial compositions of the invention.

FIG. 9. Effect of 0.1× to 10× enzyme concentration on *Xanthomonas Campestris* pathovar 14171.

FIGS. 10A and 10B show the effect of the substrate concentrations on *Xanthomonas campestris* pathovars. FIG. 10A shows schematically the placement of the enzyme assemblies under analysis. FIG. 10B shows growth inhibition at all substrate concentrations.

FIG. 11. Effect of 0.1× to 10× enzyme concentrations on the pathogenic fungus *Pythium vexans*.

FIGS. 12A and 12B show tomato seeds protected from *Pseudomonas* and *Clavibacter* pathogens by the seed coatings of the invention. The enzyme layers comprised 1× enzyme formulation and 1× substrate formulation. Seeds were in triplicate. FIG. 12A shows *Pseudomonas syringae* 14045-8b. FIG. 12B shows *Clavibacter michiganensis* 0690.

FIG. 13. The seed coatings protected tomato seeds from two pathogenic species of *Fusarium* in a distance-dependent fashion. The seed coatings comprised 1× enzyme formulation and 1× substrate formulation. Seeds were plated in triplicate and positioned at different distances from the fungal inoculum.

DETAILED DESCRIPTION OF THE INVENTION

The present invention provides compositions and methods for reducing microbial contamination or infection in plants, animals, fabrics, and products therefrom. This is accomplished, for the first time, by a solid, multicomponent composition comprising a hydrogen peroxide producing (HPP) enzyme and a free radical producing (FRP) enzyme in self-assembled magnetic nanoparticles in one component and substrates for the enzymes in another component. These magnetically-immobilized enzymes may be in solid or liquid compositions that are stable and inactive. Thus, they may be stored prior to or after incorporation into products. When the antimicrobial activities are required, these multicomponent compositions are activated by exposure to hydration and/or oxygen. The HPP enzyme acts on substrates to produce hydrogen peroxide and D-glucono-δ-lactone. The FRP enzyme acts on the hydrogen peroxide and one or more further substrates to produce free radicals. The hydrogen peroxide and free radicals have antimicrobial properties. In alternative embodiments, hydrogen peroxide is provided as opposed to a hydrogen peroxide producing enzyme plus its substates.

Self-assembled mesoporous nanoclusters comprising entrapped peroxidases are highly active and robust. The technology is a powerful blend of biochemistry, nanotechnology, and bioengineering at three integrated levels of organization: Level 1 is the self-assembly of peroxidase and oxidase enzymes with magnetic nanoparticles (MNP) for the synthesis of magnetic mesoporous nanoclusters. This level uses a mechanism of molecular self-entrapment to immobilize and stabilize enzymes. Level 2 is the stabilization of the MNPs into other matrices. Level 3 is product conditioning and packaging for Level 1+2 delivery. The assembly of magnetic nanoparticles adsorbed to enzyme is herein also referred to as a "bionanocatalyst" (BNC).

MNP immobilization provides highly active and cost-effective peroxidases. Peroxidases are very potent enzymes yet notoriously difficult to deploy in industrial settings due to strong inhibition in presence of excess peroxide. NPs increase peroxidation activity and reduce their inhibition which renders them industrially useful. Additionally, the MNPs allow for a broader range of operating conditions such as temperature, ionic strength and pH. (The size and magnetization of the MNPs affect the formation and structure of the NPs, all of which have a significant impact on the activity of the entrapped enzymes. By virtue of their surprising resilience under various reaction conditions, MNPs can be used as improved enzymatic or catalytic agents where other such agents are currently used. Furthermore, they can be used in other applications where enzymes have not yet been considered or found applicable.

The BNC contains mesopores that are interstitial spaces between the magnetic nanoparticles. The enzymes are preferably embedded or immobilized within at least a portion of mesopores of the BNC. As used herein, the term "magnetic" encompasses all types of useful magnetic characteristics, including permanent magnetic, superparamagnetic, paramagnetic, ferromagnetic, and ferrimagnetic behaviors.

The magnetic nanoparticle or BNC has a size in the nanoscale, i.e., generally no more than 500 nm. As used herein, the term "size" can refer to a diameter of the magnetic nanoparticle when the magnetic nanoparticle is approximately or substantially spherical. In a case where the magnetic nanoparticle is not approximately or substantially spherical (e.g., substantially ovoid or irregular), the term "size" can refer to either the longest dimension or an average of the three dimensions of the magnetic nanoparticle. The term "size" may also refer to an average of sizes over a population of magnetic nanoparticles (i.e., "average size").

In different embodiments, the magnetic nanoparticle has a size of precisely, about, up to, or less than, for example, 500 nm, 400 nm, 300 nm, 200 nm, 100 nm, 50 nm, 40 nm, 30 nm, 25 nm, 20 nm, 15 nm, 10 nm, 5 nm, 4 nm, 3 nm, 2 nm, or 1 nm, or a size within a range bounded by any two of the foregoing exemplary sizes.

In the BNC, the individual magnetic nanoparticles can be considered to be primary nanoparticles (i.e., primary crystallites) having any of the sizes provided above. The aggregates of nanoparticles in a BNC are larger in size than the nanoparticles and generally have a size (i.e., secondary size) of at least about 5 nm. In different embodiments, the aggregates have a size of precisely, about, at least, above, up to, or less than, for example, 5 nm, 8 nm, 10 nm, 12 nm, 15 nm, 20 nm, 25 nm, 30 nm, 35 nm, 40 nm, 45 nm, 50 nm, 60 nm, 70 nm, 80 nm, 90 nm, 100 nm, 150 nm, 200 nm, 300 nm, 400 nm, 500 nm, 600 nm, 700 nm, or 800 nm, or a size within a range bounded by any two of the foregoing exemplary sizes. [0036]

Typically, the primary and/or aggregated magnetic nanoparticles or BNCs thereof have a distribution of sizes, i.e., they are generally dispersed in size, either narrowly or broadly dispersed. In different embodiments, any range of primary or aggregate sizes can constitute a major or minor proportion of the total range of primary or aggregate sizes. For example, in some embodiments, a particular range of primary particle sizes (for example, at least about 1, 2, 3, 5, or 10 nm and up to about 15, 20, 25, 30, 35, 40, 45, or 50 nm) or a particular range of aggregate particle sizes (for example, at least about 5, 10, 15, or 20 nm and up to about 50, 100, 150, 200, 250, or 300 nm) constitutes at least or above about 50%, 60%, 70%, 80%, 90%, 95%, 98%, 99%, or 100% of the total range of primary particle sizes. In other embodiments, a particular range of primary particle sizes (for example, less than about 1, 2, 3, 5, or 10 nm, or above about 15, 20, 25, 30, 35, 40, 45, or 50 nm) or a particular range of aggregate particle sizes (for example, less than about 20, 10, or 5 nm, or above about 25, 50, 100, 150, 200, 250, or 300 nm) constitutes no more than or less than about 50%, 40%, 30%, 20%, 10%, 5%, 2%, 1%, 0.5%, or 0.1% of the total range of primary particle sizes.

The aggregates of magnetic nanoparticles (i.e., "aggregates") or BNCs thereof can have any degree of porosity, including a substantial lack of porosity depending upon the quantity of individual primary crystallites they are made of In particular embodiments, the aggregates are mesoporous by containing interstitial mesopores (i.e., mesopores located between primar magnetic nanoparticles, formed by packing arrangements). The mesopores are generally at least 2 nm and up to 50 nm in size. In different embodiments, the mesopores can have a pore size of precisely or about, for example, 2, 3, 4, 5, 10, 12, 15, 20, 25, 30, 35, 40, 45, or 50 nm, or a pore size within a range bounded by any two of the foregoing exemplary pore sizes. Similar to the case of particle sizes, the mesopores typically have a distribution of sizes, i.e., they are generally dispersed in size, either narrowly or broadly dispersed. In different embodiments, any range of mesopore sizes can constitute a major or minor proportion of the total range of mesopore sizes or of the total pore volume. For example, in some embodiments, a particular range of mesopore sizes (for example, at least about 2, 3, or 5, and up to 8, 10, 15, 20, 25, or 30 nm) constitutes at least or above about 50%, 60%, 70%, 80%, 90%, 95%, 98%, 99%, or 100% of the total range of mesopore sizes or of the total pore volume. In other embodiments, a particular range of mesopore sizes (for example, less than about 2, 3, 4, or 5 nm, or above about 10, 15, 20, 25, 30, 35, 40, 45, or 50 nm) constitutes no more than or less than about 50%, 40%, 30%, 20%, 10%, 5%, 2%, 1%, 0.5%, or 0.1% of the total range of mesopore sizes or of the total pore volume.

The magnetic nanoparticles can have any of the compositions known in the art. In some embodiments, the magnetic nanoparticles are or include a zerovalent metallic portion that is magnetic. Some examples of such zerovalent metals include cobalt, nickel, and iron, and their mixtures and alloys. In other embodiments, the magnetic nanoparticles are or include an oxide of a magnetic metal, such as an oxide of cobalt, nickel, or iron, or a mixture thereof. In some embodiments, the magnetic nanoparticles possess distinct core and surface portions. For example, the magnetic nanoparticles may have a core portion composed of elemental iron, cobalt, or nickel and a surface portion composed of a passivating layer, such as a metal oxide or a noble metal coating, such as a layer of gold, platinum, palladium, or silver. In other embodiments, metal oxide magnetic nanoparticles or aggregates thereof are coated with a layer of a noble metal coating. The noble metal coating may, for example, reduce the number of charges on the magnetic nanoparticle surface, which may beneficially increase dispersibility in solution and better control the size of the BNCs. The noble metal coating protects the magnetic nanoparticles against oxidation, solubilization by leaching or by chelation when chelating organic acids, such as citrate, malonate, or tartrate, are used in the biochemical reactions or processes. The passivating layer can have any suitable thickness, and particularly, at least, up to, or less than, about for example, 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, or 10 nm, or a thickness in a range bounded by any two of these values.

Magnetic materials useful for the invention are well-known in the art. Non-limiting examples comprise ferromagnetic and ferromagnetic materials including ores such as iron ore (magnetite or lodestone), cobalt, and nickel. In other embodiments, rare earth magnets are used. Non-limiting examples include neodymium, gadolinium, sysprosium, samarium-cobalt, neodymium-iron-boron, and the like. In yet further embodiments, the magnets comprise composite materials. Non-limiting examples include ceramic, ferrite, and alnico magnets. In preferred embodiments, the magnetic nanoparticles have an iron oxide composition. The iron oxide composition can be any of the magnetic or superparamagnetic iron oxide compositions known in the art, e.g., magnetite ($Fe_sO/O$, hematite ($\alpha$-Fe2$\theta$ 3), maghemite ($\gamma$-Fe2C>3), or a spinel ferrite according to the formula $AB_2O_4$, wherein A is a divalent metal (e.g., $Xn^{2+}$, $Ni^{2+}$, $Mn_{2+}$, $Co^{2+}Ba^{2+}$, $Sr^{2+}$, or combination thereof) and B is a trivalent metal (e.g., $Fe^{3+}$, $CO^{3+}$, or combination thereof).

The individual magnetic nanoparticles or aggregates thereof or BNCs thereof possess any suitable degree of magnetism. For example, the magnetic nanoparticles, BNCs, or BNC scaffold assemblies can possess a saturated magnetization (Ms) of at least or up to about 5, 10, 15, 20, 25, 30, 40, 45, 50, 60, 70, 80, 90, or 100 emu/g. The magnetic nanoparticles, BNCs, or BNC-scaffold assemblies preferably possess a remanent magnetization (Mr) of no more than (i.e., up to) or less than 5 emu/g, and more preferably, up to or less than 4 emu/g, 3 emu/g, 2 emu/g, 1 emu/g, 0.5 emu/g, or 0.1 emu/g. The surface magnetic field of the magnetic nanoparticles, BNCs, or BNC-scaffold assemblies can be about or at least, for example, about 0.5, 1, 5, 10, 50, 100, 200, 300, 400, 500, 600, 700, 800, 900, or 1000 Gauss (G), or a magnetic field within a range bounded by any two of the foregoing values. If microparticles are included, the microparticles may also possess any of the above magnetic strengths.

The magnetic nanoparticles or aggregates thereof can be made to adsorb a suitable amount of enzyme, up to or below a saturation level, depending on the application, to produce the resulting BNC. In different embodiments, the magnetic nanoparticles or aggregates thereof may adsorb about, at least, up to, or less than, for example, 1, 5, 10, 15, 20, 25, or 30 pmol/m2 of enzyme. Alternatively, the magnetic nanoparticles or aggregates thereof may adsorb an amount of enzyme that is about, at least, up to, or less than, for example, about 10%, 20%, 30%, 40%, 50%, 60%, 70%, 80%, 90%, or 100% of a saturation level.

The antimicrobial assemblies of the invention may be effective against a wide array of pathogens. In some embodiments, the pathogens include Phatogenic plant bacteria species such as *Acidovorax avenae, Agrobacterium tumefaciens, Burkholderia andropogonis, Burkholderia caryophylli, Burkholderia glumae, Candidatus Liberibacter, Candidatus Phytoplasma solani, Clavibacter michiganensis, Dickeya dadantii, Erwinia psidii, Pectobacterium atrosepticum, Pectobacterium betavasculorum, Pectobacterium carotovorum, Pectobacterium carotovorum* subsp. *betavasculorum, Pectobacterium wasabiae, Phytoplasma, Pseudomonas amygdali, Pseudomonas asplenii, Pseudomonas caricapapayae, Pseudomonas cichorii, Pseudomonas coronafaciens, Pseudomonas corrugate, Pseudomonas ficuserectae, Pseudomonas flavescens, Pseudomonas fuscovaginae, Pseudomonas helianthi, Pseudomonas marginalis, Pseudomonas oryzihabitans, Pseudomonas palleroniana, Pseudomonas papaveris, Pseudomonas salomonii, Pseudomonas savastanoi, Pseudomonas syringae, Pseudomonas tomato, Pseudomonas turbinellae, Pseudomonas viridiflava, Psyllid yellows, Ralstonia solanacearum Rhodococcus fascians, Spiroplasma citri, Xanthomonas axonopodis, Xanthomonas campestris, Xanthomonas campestris, Xanthomonas oryzae,* and *Xylella fastidiosa.*

In other embodiments, the antimicrobial assemblies are effective against non-plant pathogen bacteria including *Escherishia coli, Brucella* sp., *Vibrio* sp., *Serrati asp., Nocardia* sp., *Leptospira* sp., *Mycobacterium* sp., *Clostridium* sp., *Bacillus* sp., *Pseudomonas* sp. *Staphylococcus* sp., *Neisseria* sp., *Haemophilus* sp., *Helicobacter* sp., *Mycoplasma* sp., *Pseudomonas* sp. *Treponema* sp., and *Yersinia* sp.

In other embodiments, the antimicrobial assemblies are effective against plant pathogen Fungi including genera such as *Ascidium* sp., *Alternaria* sp., *Armillaria* sp. *Ascochyta* sp., *Aspergillus* sp., *Bipoloaris, Bjerkandera* sp., *Botrytis* sp., *Ceratobasidium* sp., *Cercospora* sp., *Chrysimyxa* sp., *Cladosporium* sp., *Cochliobolus* sp., *coleosporium* sp., *Colletotrichum* sp., *Cylindrocladium* sp., *Cytospora* sp., *Diaporthe* sp., *Didymella* sp., *Drechslera* sp., *Erysiphe* sp, *Exobasidium* sp., *Fusarium* sp., *Ganoderma* sp., *Gibberellasp., Gymnospragium* sp., *Helicobasidium* sp., *Inonotus* sp., *Leptosphaeria* sp., *Leucostoma* sp. *Marasmius* sp., *Microspaera* sp., *Mucor* sp., *Mycosphaerella* sp., *Nectria* sp., *Oidium* sp., *Passalora* sp., *Pestalotiopsis* sp., *Phaeoramularia* sp., *Phoma* sp., *Phyllostica* sp., *Phytophtora* sp., *Pseudocercospora* sp., *Puccini* asp., *Pyrenophora* sp., *Rhizoctonia* sp., *rhizopus* sp., *Septoria* sp., *Sphaceloma* sp., *Stemphylium* sp., *Stigmina* sp., *Tilletia* sp., *Typhula* sp., *Uromyces* sp., *Ustilago* sp., *Verticillium* sp.

In other embodiments, the invention is effective against plant viruses that include plant viruses such as Mosaic Viruses, Mottle Viruses, Begomoviruses, Carlaviruses, Carmoviruses, Criniviruses, Fabaviruses, Furoviruses, Machlomoviruses, Macluraviruses, Necroviruses, Potexviruses, Tenuiviruses, and Tospoviruses.

The magnetic nanoparticles or aggregates thereof or BNCs thereof possess any suitable pore volume. For example, the magnetic nanoparticles or aggregates thereof can possess a pore volume of about, at least, up to, or less than, for example, about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm3/g, or a pore volume within a range bounded by any two of the foregoing values.

The magnetic nanoparticles or aggregates thereof or BNCs thereof possess any suitable specific surface area. For example, the magnetic nanoparticles or aggregates thereof can have a specific surface area of about, at least, up to, or less than, for example, about 50, 60, 70, 80, 90, 100, 110, 120, 130, 140, 150, 160, 170, 180, 190, or 200 m2/g.

MNPs, their structures, organizations, suitable enzymes, and uses are described in WO2012122437 and WO2014055853, incorporated by reference herein in their entirety.

In some embodiments, the invention provides hydrogen peroxide producing (HPP) enzymes. In certain embodiments, the HPP enzymes are oxidases that may be of the EX 1.1.3 subgenus. In particular embodiments, the oxidase may be EC 1.1.3.3 (malate oxidase), EC 1.1.3.4 (glucose oxidase), EC 1.1.3.5 (hexose oxidase), EC 1.1.3.6 (cholesterol oxidase), EC 1.1.3.7 (aryl-alcohol oxidase), EC 1.1.3.8 (L-gulonolactone oxidase), EC 1.1.3.9 (galactose oxidase), EC 1.1.3.10 (pyranose oxidase), EC 1.1.3.11 (L-sorbose oxidase), EC 1.1.3.12 (pyridoxine 4-oxidase), EC 1.1.3.13 (alcohol oxidase), EC 1.1.3.14 (catechol oxidase), EC 1.1.3.15 (2-hydroxy acid oxidase), EC 1.1.3.16 (ecdysone oxidase), EC 1.1.3.17 (choline oxidase), EC 1.1.3.18 (secondary-alcohol oxidase), EC 1.1.3.19 (4-hydroxymandelate oxidase), EC 1.1.3.20 (long-chain alcohol oxidase), EC 1.1.3.21 (glycerol-3-phosphate oxidase), EC 1.1.3.22, EC 1.1.3.23 (thiamine oxidase), EC 1.1.3.24 (L-galactonolactone oxidase), EC 1.1.3.25, EC 1.1.3.26, EC 1.1.3.27 (hydroxyphytanate oxidase), EC 1.1.3.28 (nucleoside oxidase), EC 1.1.3.29 (Nacylhexosamine oxidase), EC 1.1.3.30 (polyvinyl alcohol oxidase), EC 1.1.3.31, EC 1.1.3.32, EC 1.1.3.33, EC 1.1.3.34, EC 1.1.3.35, EC 1.1.3.36, EC 1.1.3.37 D-arabinono-1,4-lactone oxidase), EC 1.1.3.38 (vanillyl alcohol oxidase), EC 1.1.3.39 (nucleoside oxidase, $H_2O_2$ forming), EC 1.1.3.40 (D-mannitol oxidase), or EC 1.1.3.41 (xylitol oxidase).

The invention provides Free Radical Producing (FRP) enzymes in one of the sequential components of the solid antimicrobial compositions. In some embodiments, the FRP is a peroxidase. Peroxidases are widely found in biological systems and form a subset of oxidoreductases that reduce hydrogen peroxide ($H_2O_2$) to water in order to oxidize a large variety of aromatic compounds ranging from phenol to aromatic amines.

Peroxidases belong of the sub-genus EC 1.11.1. In certain embodiments, the EC 1.11.1 enzyme is The EC 1.11.1 enzyme can be more specifically, for example, EC 1.11.1.1 (NADH peroxidase), EC 1.11.1.2 (NADPH peroxidase), EC 1.11.1.3 (fatty acid peroxidase), EC 1.11.1.4, EC 1.11.1.5 (cytochrome-c peroxidase), EC 1.11.1.6 (catalase), EC 1.11.1.7 (peroxidase), EC 1.11.1.8 (iodide peroxidase), EC 1.11.1.9 (glutathione peroxidase), EC 1.11.1.10 (chloride peroxidase), EC 1.11.1.11 (L-ascorbate peroxidase), EC 1.11.1.12 (phospholipid-hydroperoxide glutathione peroxidase), EC 1.11.1.13 (manganese peroxidase), EC 1.11.1.14 (diarylpropane peroxidase), or EC 1.11.1.15 (peroxiredoxin).

In other embodiments, the peroxidase may also be further specified by function, e.g., a lignin peroxidase, manganese peroxidase, or versatile peroxidase. The peroxidase may also be specified as a fungal, microbial, animal, or plant peroxidase. The peroxidase may also be specified as a class I, class II, or class III peroxidase. The peroxidase may also be specified as a myeloperoxidase (MPO), eosinophil peroxidase (EPO), lactoperoxidase (LPO), thyroid peroxidase (TPO), prostaglandin H synthase (PGHS), glutathione peroxidase, haloperoxidase, catalase, cytochrome c peroxidase, horseradish peroxidase, peanut peroxidase, soybean peroxidase, turnip peroxidase, tobacco peroxidase, tomato peroxidase, barley peroxidase, or peroxidasin. In these particular embodiments, the peroxidase is a lactoperoxidase.

The lactoperoxidase/glucose oxidase (LP/GOX) antimicrobial system occurs naturally in bodily fluids such as milk, saliva, tears, and mucous (Bosch et al., *J. Applied Microbiol.*, 89(2), 215-24 (2000)). This system utilizes thiocyanate (SCN—) and iodide (I—), two naturally occurring compounds that are harmless to mammals and higher organisms (Welk et al. *Archives of Oral Biology*, 2587 (2011)). LP catalyzes the oxidation of thiocyanate and iodide ions into hypothiocyanite (OSCN—) and hypoiodite (OI—), respectively, in the presence of hydrogen peroxide ($H_2O_2$). The $H_2O_2$ in this system is provided by the activity of GOX on β-D-glucose in the presence of oxygen. These free radical compounds, in turn, oxidize sulfhydryl groups in the cell membranes of microbes (Purdy, Tenovuo et al. *Infection and Immunity*, 39(3), 1187 (1983); Bosch et al., *J. Applied Microbiol.*, 89(2), 215-24 (2000), leading to impairment of membrane permeability (Wan, Wang et al. *Biochemistry Journal*, 362,355-362 (2001)) and ultimately microbial cell death. Concentrations as low as 20 μM of hypothiocyanite and hypoiodite can result in inhibition of cell growth (Bosch, van Doorne et al. 2000). The LP/GOX system is effective on thiocyanate on its own; when paired with iodide, there is a synergistic effect that enhances biostatic and biocidal activity and extends the susceptible target range including Gram negative bacteria (e.g., *E. coli, P. aerugenosa*), Gram positive bacteria (e.g., *S. aureus, Streptococcus* spp.), and fungus (e.g., *C. albicans*) (Reiter, Marshall et al. *Infection and Immunity*, 13(3), 800-807 (1976); Bosch et al., *J. Applied Microbiol.*, 89(2), 215-24 (2000); Welk et al. *Archives of Oral Biology*, 2587 (2011).) Furthermore, the LP/GOX system functions in two phases: (1) the generation and action of hypothiocyanite and hypoiodite on cell membranes, and then, when these compounds are depleted, (2) excess $H_2O_2$ builds up, enacting its own oxidative damage on cellular structures (Reiter, Marshall et al. 1976). The forgoing references are incorporated herein by reference in their entirety.

The enzyme system has been deployed and approved in the industry for biofilm control such as toothpaste and milk anti-spoiling agents. The system is largely non-specific and robust with few reaction requirements. One study found persistent biostatic and biocidal activity against Gram (−) and (+) bacteria and *C. albicans* after 18 months of reinoculation every two months Bosch et al., *J. Applied Microbiol.*, 89(2), 215-24 (2000). The effective pH range is 3-7 with a peak LP activity at pH 5 (Reiter, Marshall et al. 1976; Purdy, Tenovuo et al. 1983). Higher activity is typically witnessed against bacteria at pH 3, but this is likely due to inhibition of growth by low pH (Reiter, Marshall et al. 1976). Other than pH, the only strict requirement for activity of the LP/GOX system is the presence of oxygen, without which GOX can't generate $H_2O_2$ from glucose. The forgoing references are incorporated herein by reference in their entirety.

LP/GOX has been described as a pesticide for microorganisms that include bacteria and fungi. (See U.S. Pat. No. 6,447,811, incorporated by reference herein in its entirety). Thus, in some embodiments, the invention described herein provides magnetically-immobilized pesticides in solid or liquid formulations. The pesticides comprise a peroxidase enzyme that produces a free radical. In some embodiments, the peroxidase enzyme is lactoperoxidase. The pesticides further comprise a peroxide source that may include an enzyme that oxidizes glucose.

The invention provides inactive magnetically-immobilized enzymes. The enzymes may be inactive because they are not exposed to water, oxygen, substrates, or any combination thereof. In a preferred embodiment of the present invention, the magnetically-immobilized enzymes are in an oil base. This limits enzymatic activity prior to use. Activation of the immobilized enzymes occurs upon exposure to hydration and/or oxygen. In a more preferred embodiment, the magnetically-immobilized enzymes are in an oil base comprising an agent for emulsifying the oil in an aqueous solution to form an oil-in-water emulsion. In another more preferred embodiment, the oil is a mineral oil, vegetable oil, or animal oil. Exemplary mineral oils include paraffin oil and kerosene-type oils. Exemplary animal oils include fish oils such as herring and mackerel oil. Examples of vegetable oils are peanut oil, sesame oil, rape-seed oil, linseed oil, castor oil, soybean oil, corn germ oil, and cotton-seed oil.

In other embodiments, in order to further facilitate the distribution of the magnetically-immobilized enzymes over a surface, one or more spreading agents known in the art can further be added to the composition or the oil base. In some embodiments, the spreading agents are non-ionogenic surface tension-reducing substances. In preferred embodiments, the spreading agents are ethoxylated alcohols and phosphatidyl lipids.

In other embodiments, one or more adhesives can be added. Adhesives may help prevent the magnetically-immobilized enzymes from being rinsed off the plant by rain or other conditions. Adhesives are well known in the art. Examples are starch, gums such as xanthan gum, gum Arabic and carboxymethyl celluloses (CMCs).

The composition can be applied by means of spraying, sprinkling, atomizing, overhead spraying, watering, immersing, and drip irrigation. A particularly advantageous method for applying the composition is spraying both by means of low volume methods (mist systems) and high volume methods. Drip irrigation can be used for culture systems on rockwool and other growth substrates. The magnetically-immobilized enzymes according to the invention can also be used to disinfect drip irrigation systems. In both latter cases the presence of the oil base is not strictly necessary for an optimal activity. Immersion in a bath with the composition is particularly suitable for the treatment of plant parts, in particular harvestable parts, such as bulbs, tubers, fruits and the like.

The magnetically-immobilized enzymes can be made commercially available in different forms. In a preferred embodiment, the peroxidase activity is delayed as long as possible because this increases the shelf-life of the product. The enzymatic activity starts upon exposure to both hydration (i.e. water) and oxygen. In the present case the glucose oxidase/glucose system is the hydrogen peroxide donor. In more preferred embodiments, the hydrogen peroxide donor is provided separately from the peroxidase. In addition, the oil base and the spreading agent can, if desired, also be packaged separately.

In another embodiment, a kit is provided for forming the composition the kit comprises an optionally concentrated enzyme composition comprising a peroxidase (e.g. lactoperoxidase) and a hydrogen peroxide donor (e.g. glucose oxidase and glucose). In preferred embodiments, the kit may further comprise thiocyanate, iodide, oil, an emulsifier, or spreading agents. In more preferred embodiments, the ingredients are mixed with each other before use. In another embodiment, the kit may comprise one or more ingredients in a concentrated form for dilution or hydration prior to or concurrently with use.

In embodiments where β-D-Glucose is oxidized to $H_2O_2$, or where cellulose derived sugars are oxidized to $H_2O_2$, cellulase enzymes may be provided with the compositions of the invention. In some embodiments, the seed coating further comprises the cellulase.

In some embodiments, the cellulases are exocellulases, endocellulases, hemicellulases, or combinations thereof known in the art. Endocellulase (EC 3.2.1.4) randomly cleaves internal bonds at amorphous sites that create new chain ends. Exocellulase (EC 3.2.1.91) cleaves two to four units from the ends of the exposed chains produced by endocellulase, resulting in the tetrasaccharides or disaccharides, such as cellobiose. There are two main types of exocellulases [or cellobiohydrolases (CBH)]-CBHI works processively from the reducing end, and CBHII works processively from the nonreducing end of cellulose. Cellobiase (EC 3.2.1.21) or beta-glucosidase hydrolyses the exocellulase product into individual monosaccharides. Oxidative cellulases depolymerize cellulose by radical reactions, as for instance cellobiose dehydrogenase (acceptor). Cellulose phosphorylases depolymerize cellulose using phosphates instead of water.

In other embodiments, endocellulases may include EC 3.2.1.4, endo-1,4-beta-D-glucanase, beta-1,4-glucanase, beta-1,4-endoglucan hydrolase, celluase A, cellulosin AP, endoglucanase D, alkali cellulase, cellulase A 3, celludextrinase, 9.5 cellulase, avicelase, pancellase SS, and 1,4-(1,3,1,4)-beta-D-glucan 4-glucanohydrolase). Cellulases enzymes are typically produced by fungi, bacteria, and protozoans of cellulose). Other names for 'endoglucanases' are: endo-1,4-beta-glucanase, carboxymethyl cellulase (CMCase), endo-1,4-beta-D-glucanase, beta-1,4-glucanase, beta-1,4-endoglucan hydrolase, and celludextrinase.

In some embodiments, the methods described herein use recombinant cells that express the enzymes used in the invention. Recombinant DNA technology is known in the art. In some embodiments, cells are transformed with expression vectors such as plasmids that express the enzymes. In other embodiments, the vectors have one or more genetic signals, e.g., for transcriptional initiation, transcriptional termination, translational initiation and translational termination. Here, nucleic acids encoding the enzymes may be cloned in a vector so that it is expressed when properly transformed into a suitable host organism.

Suitable host cells may be derived from bacteria, fungi, plants, or animals as is well-known in the art.

In some embodiments, the invention provides that the matrix material is a biopolymer. Examples include the polysaccharides (e.g., cellulose, hemicellulose, xylan, chitosan, inulin, dextran, agarose, and alginic acid), polylactic acid, and polyglycolic acid. In other embodiments, the matrix material is a water-soluble cellulose derivative, a water-solvatable cellulose derivative, an alginate derivative, and a chitosan derivative.

In some embodiments, the matrix comprises cellulose. Cellulose is an organic compound with the formula $(C_6H_{10}O_5)n$, a polysaccharide consisting of a linear chain of several hundred to many thousands of $\beta(1\rightarrow 4)$ linked D-glucose units. The cellulose used in the invention may be obtained or derived from plant, algal, or microbial sources. In some embodiments, the invention provides cellulose derivatives known in the art. The hydroxyl groups (—OH) of cellulose can be partially or fully reacted with reagents known in the art. In preferred embodiments, the cellulose derivatives are cellulose esters and cellulose ethers (—OR). In more preferred embodiments, the cellulose derivatives are cellulose acetate, cellulose triacetate, cellulose proprionate, cellulose acetate proprionate (CAP), cellulose acetate butyrate (CAB), nitrocellulose (cellulose nitrate), cellulose sulfate, methylcellulose, ethylcellulose, ethyl methyl cellulose, hydroxyethyl cellulose, hydroxypropyl cellulose (HPC), hydroxyethyl methyl cellulose, hydroxypropyl methyl cellulose (HPMC), ethyl hydroxyethyl cellulose, and carboxymethyl cellulose (CMC).

In some embodiments, the matrix comprises carboxymethyl cellulose. Carboxymethyl cellulose (CMC) or cellulose gum [1] is a cellulose derivative with carboxymethyl groups (—CH2—COOH) bound to some of the hydroxyl groups of the glucopyranose monomers that make up the cellulose backbone. It is synthesized using techniques known in the art, e.g., by the alkali-catalyzed reaction of cellulose with chloroacetic acid. The polar (organic acid) carboxyl groups render the cellulose soluble and chemically reactive. The functional properties of CMC depend on the degree of substitution of the cellulose structure (i.e., how many of the hydroxyl groups have taken part in the substitution reaction), as well as the chain length of the cellulose backbone structure and the degree of clustering of the carboxymethyl substituents.

In some embodiments, the matrix comprises hydroxypropyl cellulose (HPC). HPC is a derivative of cellulose with both water solubility and organic solubility. HPC is an ether of cellulose in which some of the hydroxyl groups in the repeating glucose units have been hydroxypropylated forming —OCH2CH(OH)CH3 groups using propylene oxide. The average number of substituted hydroxyl groups per glucose unit is referred to as the degree of substitution (DS). Complete substitution would provide a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3. Because cellulose is very crystalline, HPC must have an MS about 4 in order to reach a good solubility in water. HPC has a combination of hydrophobic and hydrophilic groups, so it has a lower critical solution temperature (LCST) at 45° C. At temperatures below the LCST, HPC is readily soluble in water; above the LCST, HPC is not soluble. HPC forms liquid crystals and many mesophases according to its concentration in water. Such mesophases include isotropic, anisotropic, nematic and cholesteric. The last one gives many colors such as violet, green and red.

In some embodiments, the matrix comprises methyl cellulose. Methyl cellulose (or methylcellulose) is derived from cellulose. It is a hydrophilic white powder in pure form and dissolves in cold (but not in hot) water, forming a clear viscous solution or gel. Methyl cellulose does not occur naturally and is synthetically produced by heating cellulose with caustic solution (e.g. a solution of sodium hydroxide) and treating it with methyl chloride. In the substitution reaction that follows, the hydroxyl residues (—OH functional groups) are replaced by methoxide (—OCH$_3$ groups).

Different kinds of methyl cellulose can be prepared depending on the number of hydroxyl groups substituted. Cellulose is a polymer consisting of numerous linked glucose molecules, each of which exposes three hydroxyl groups. The Degree of Substitution (DS) of a given form of methyl cellulose is defined as the average number of substituted hydroxyl groups per glucose. The theoretical maximum is thus a DS of 3.0, however more typical values are 1.3-2.6.

In some embodiments, the matrix comprises alginate. Alginate, also called Alginic acid, and algin, is an anionic polysaccharide distributed widely in the cell walls of brown algae. When bound with water it forms a viscous gum. In extracted form it absorbs water quickly; it is capable of absorbing 200-300 times its own weight in water. It is sold in filamentous, granular or powdered forms. The invention provides matrix materials of known alginate and alginate-derived materials. In preferred embodiments, the alginate-derived materials include alginate-polylysine-alginate (APA), Alginate/Poly-1-lysine/Pectin/Poly-1-lysine/Alginate (APPPA), Alginate/Poly-1-lysine/Pectin/Poly-1-lysine/Pectin (APPPP), and Alginate/Poly-L-lysine/Chitosan/Poly-1-lysine/Alginate (APCPA), alginate-polymethylene-co-guanidine-alginate (A-PMCG-A), hydroxymethylacrylate-methyl methacrylate (HEMA-MMA), multilayered HEMA-MMA-MAA, polyacrylonitrile-vinylchloride (PAN-PVC).

In some embodiments, the matrix comprises chitosan. Chitosan is a linear polysaccharide composed of randomly distributed β-(1-4)-linked D-glucosamine (deacetylated unit) and N-acetyl-D-glucosamine (acetylated unit). The amino group in chitosan has a pKa value of ~6.5, which leads to a protonation in acidic to neutral solution with a charge density dependent on pH and the % DA-value. This makes chitosan water soluble and a bioadhesive which readily binds to negatively charged surfaces such as mucosal membranes. It is produced commercially by deacetylating chitin, which is the structural element in the exoskeleton of crustaceans (such as crabs and shrimp) and cell walls of fungi, with sodium hydroxide. Chitosan is used in agriculture as a seed treatment and biopesticide. In winemaking, it is used as a fining agent, also helping to prevent spoilage. It is also used in bandages to reduce bleeding and as an antibacterial agent. It is also be used to help deliver drugs through the skin.

In other embodiments, the matrix materials may be acrylonitrile/sodium methallylsuflonate, (AN-69), polyethylene glycol/poly pentamethylcyclopentasiloxane/polydimethylsiloxane (PEG/PD5/PDMS), poly JVjiV-dimethyl acrylamide (PDMAAm), siliceous encapsulates, and cellulose sulphate/sodium alginate/polymethylene-co-guanidine (CS/A/PMCG).

In some embodiments, the invention provides antimicrobial compositions that are used, inter alia, for seed coatings. Any seeds that are vulnerable to pathogens that respond to the enzyme systems disclosed herein would benefit. In some embodiments, the seeds may be for vegetables, fruits, field crops, and flowers. In other embodiments, the invention provides antimicrobial compositions that are used, inter alia, for bedding for industrially or commercially relevant domesticated animals and products derived therefrom. Many domesticated animals are known in the art. In other embodiments, the invention provides antimicrobial compositions that are used, inter alia, for wound dressings. Many wound dressings are known in the art. The invention provides fabrics that resist pathogens or contaminants that respond to the enzyme systems disclosed herein. The fabrics comprise the antimicrobial compositions described herein.

Some embodiments of the invention provides compositions and methods for reducing human infections. This is accomplished, for the first time, by a multicomponent composition comprising a hydrogen peroxide producing (HPP) enzyme and a free radical producing (FRP) enzyme in magnetic nanoparticles in one component and substrates for the enzymes in another component. The solid compositions are stable and inactive. Thus, they may be stored prior to or after incorporation into products. When the antimicrobial activities are required, the multicomponent compositions are activated by hydration. The HPP enzyme acts on substrates to produce hydrogen peroxide and D-glucono-δ-lactone. The FRP enzyme acts on the hydrogen peroxide and one or more further substrates to produce free radicals. The hydrogen peroxide and free radicals have antimicrobial properties.

In order that the invention described herein may be more fully understood, the following examples are set forth. It should be understood that these examples are for illustrative purposes only and are not to be construed as limiting this invention in any manner.

EXAMPLES

Example 1

Optimization of Magnetic Nanoparticle Immobilized HPP and FRP Enzymes

Soybean peroxidase-based (SBP), a free radical producing enzyme (FRP), was used as a catalyst in BNPs. The BNPs removed phenol from solution by converting it to polyphenol that was removed by filtration or centrifugation. The optimal conditions for SBP (i.e., BNP concentration and pH) was determined as follows:

A soybean peroxidase plus glucose oxidase (SBP/GOX) enzyme system was combined and co-immobilized in nanoparticles clusters. In order to eliminate the need for hydrogen peroxide in the substrate buffer, glucose oxidase (GOX), in the presence of oxygen and beta-D-glucose, can be used to provide hydrogen peroxide for a combined peroxidase catalyst. A modified high-throughput microplate-based assay was used to screen peroxidase catalyst (HRP, SBP or a combination thereof) with different amounts of GOX. 50 mM glucose was used for $H_2O_2$ generation. The total peroxidase concentration was kept at 60 nM for the screening and different concentrations of GOX were tested (600 nM, 60 nM, and 6 nM GOX). The three-enzyme system consisting of equal parts SBP:HRP:GOX immobilized in 240 mg/ml material had the highest free radical generation activity as compared to the 10× and 0.1× GOX:peroxidase systems.

Figure 2:
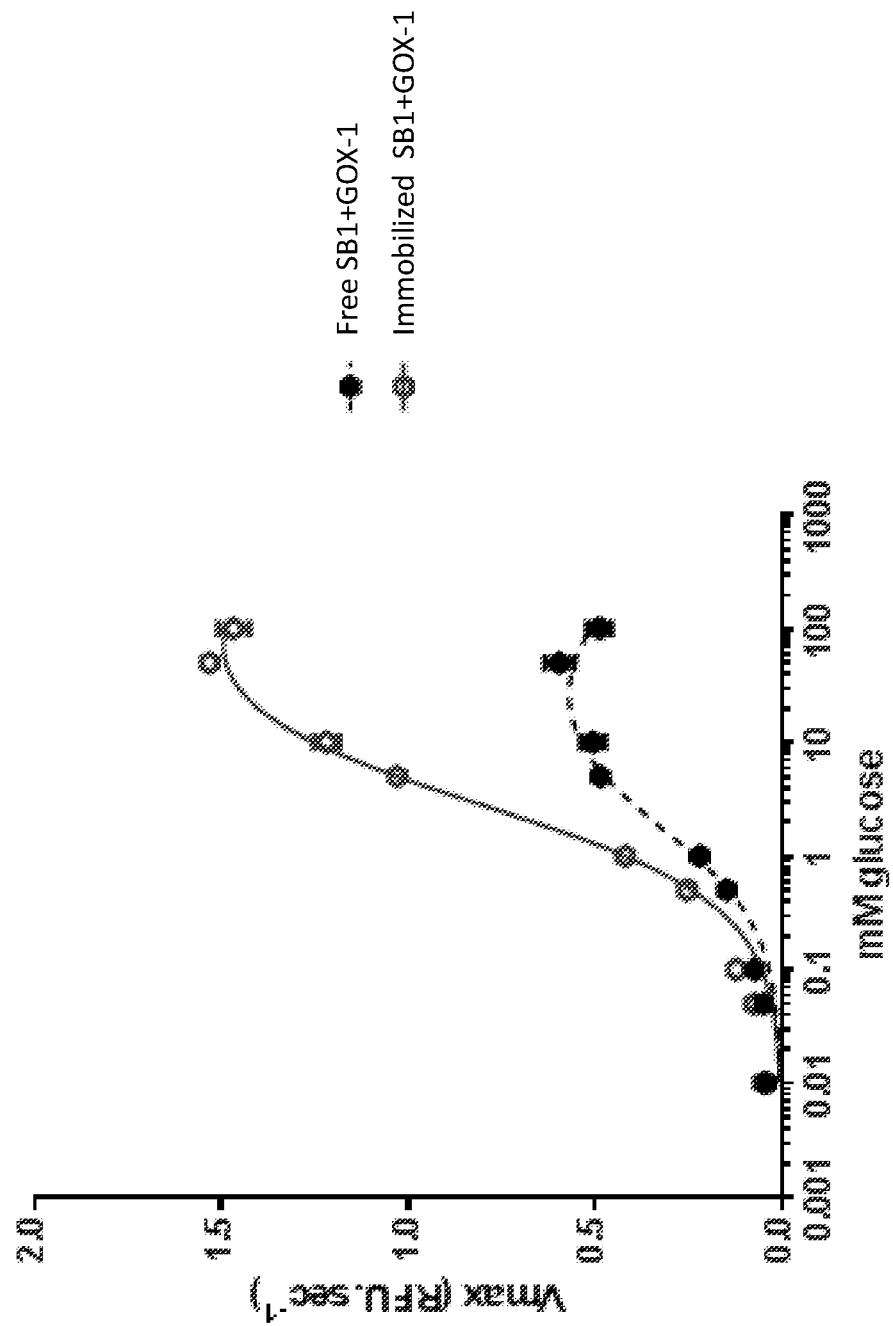

Using the optimized conditions as determined above, peroxidase activity using glucose to generate $H_2O_2$ showed a 3× increase of activity compared to the free system. This system is used to narrow the screening conditions (pH, ionic strength, concentration and time) for any peroxidase to form efficient immobilized enzyme clusters Having determined the best preparation conditions and ratios of SBP, HRP, and GOX for the three-enzyme system, the system was screened against beta-D-glucose concentrations (FIG. 2) of 10, 50, and 100 mM glucose to generate hydrogen peroxide. The phenol concentration was increased to 1 mM. Unreacted phenol was measured at $OD_{270}$ after removal of the polymerized pellet by centrifugation. After 3 hours, 10 mM glucose showed the most activity. This suggested that very high concentrations of glucose relative to free radical substrates are unnecessary. While glucose should remain in excess compared to the other substrates, its concentration in this system can possibly be dropped further below 10 mM concentration for a stoichiometric reaction with the free radical generating substrates.

Using the system described above, optimized lactoperoxidase ("LP" or "LCP") immobilization conditions were determined. Optimized LP/GOX conditions in liquid media for killing E. coli was established using hydrogen peroxide as an oxidant (LCP, FIG. 3A) or LCP plus GOX using glucose as an oxidant (LCP:GOX, FIG. 3B). Different ratios of LP:GOX were tested with 125 nM:25 nM, 125 nM:12.5 nM 125 nM:6.25 nM respectively.

The mixed enzymes were immobilized with 125, 250 or 500 μg/ml of magnetic nanoparticles. Fresh 50 μl of E. coli cells (final concentration $10^6$ cells/ml) were distributed in a 96-well microplate and incubated with 30 μl of the immobilized enzyme solutions, 20 μl SCN (0.02M)/20 μl $H_2O_2$ (Peroxide as an oxidant: 1M, 0.1M, 0.01M) or 20 μl SCN (0.02M)/20 μl glucose (Glucose as an oxidant: 1M, 0.1M, 0.01M). 100 μl of 100 mM PBS buffer was added for a final volume of 200 μl. Controls included non-immobilized enzymes, reagents alone, and 70% ethanol for 100% killing controls. All treatments were performed in triplicate.

After incubation, the microplate was centrifuged to recover the cells. The cells were then transferred to a fluorescent plate for LIVE/DEAD staining. The LIVE/DEAD® BacLight™ Bacterial Viability Kits (Life Technologies, Cat. No. L-7007) provide two different nucleic acid probes that were used to rapidly distinguish live bacteria with intact plasma membranes from dead bacteria with compromised membranes. Fluorescent counts were measure with a fluorescent plate reader (Biotek). A standard curve of live and dead cells (following ethanol treatment) was used to quantify the number of dead cells. The efficacy of the treatments was assessed as the ratio of live bacteria over dead bacteria after 5 min exposure to the immobilized enzyme formula.

Figure 3A:
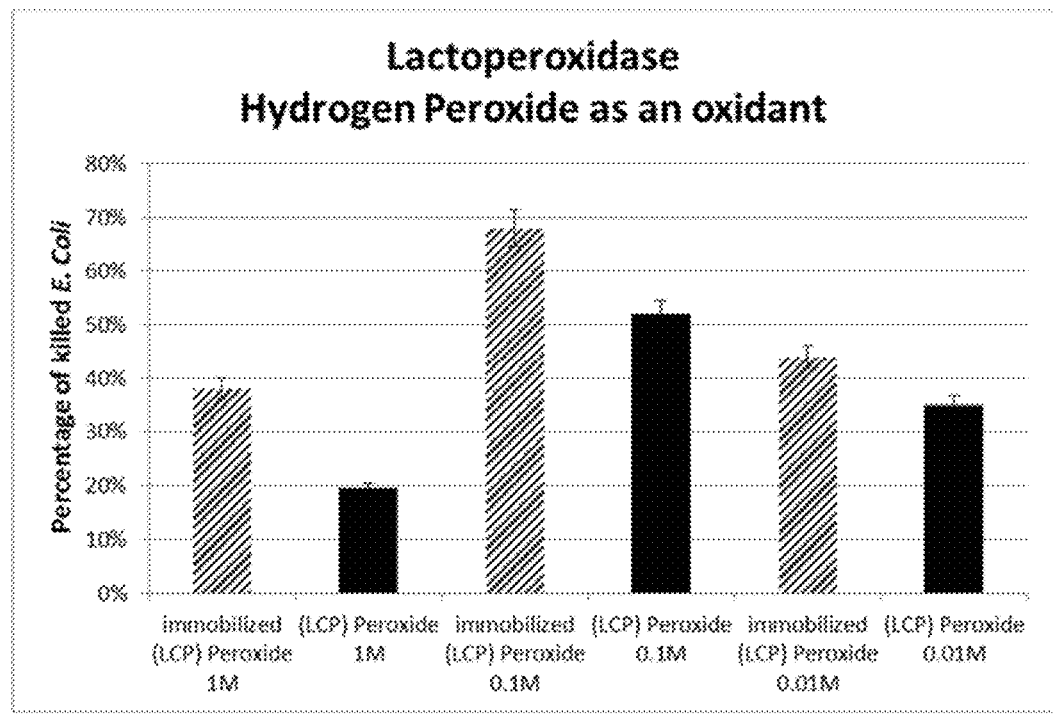
Figure 3B:
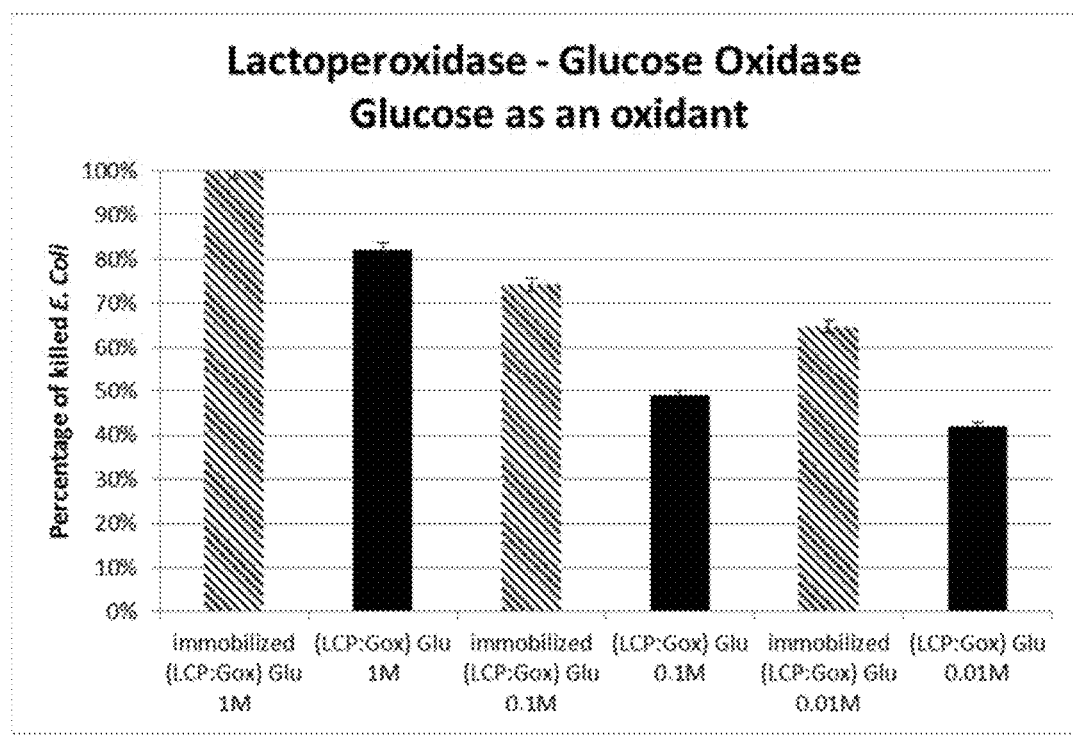

The highest efficacy for immobilized LP alone (125 nM enzyme: 500 μg/ml NP) was found to be with 20 μl of 0.1M $H_2O_2$ (10 mM final concentration) with about 68% of cells killed in 5 min (FIG. 3A). The efficacy was 100% at 5 min when immobilized LP:GOX (125 nM of LP: 25 nM of GOX: 500 μg/ml of NP) was used with 20 μl of 1M of glucose (100 mM final concentration) (FIG. 3B). In all cases, immobilized enzymes were found to have higher efficacy than their non-immobilized counterparts.

Example 2

Generation of Solid Antimicrobial LP/GOX Assemblies

The LP/GOX system, including FRP substrates, was compartmentalized in a solid antimicrobial assembly that stabilized the activity by preventing GOX from consuming glucose and producing $H_2O_2$ in the presence of oxygen. The compartmentalized reagents were formulated into a multi-layered coating assembly (Level 2) so that the formula only activated when wet and the substrates were allowed to diffuse to the enzymes. LP/GOX is a nonspecific antimicrobial system that generates hyporadicals for microbiostatic and microbicidal activity. This can be applied in novel plant seed coatings as described herein that prevents loss of viable seeds due to the action of soil-borne plant pathogens.

Discs of 2 mm for each layer were made by drying out 20 μl of solutions of Layer 1 or Layer 2. The water activated discs were composed of immobilized enzyme, substrate, and a cellulosic matrix that holds them together. The first layer contained immobilized LCP/GOX, the substrates KI and KSCN, and blue food coloring. The second layer contained glucose, KI, KSCN, and yellow food coloring. The former are blue enzyme/substrate dots, and the latter are yellow substrate only dots. Both were prepared in a viscous solution of carboxymethylcellulose (CMC) that was pipetted onto wax film (for easy removal) and allowed to dry for 24 h, leaving small concentrated disks of their respective components. Yellow and blue dots are stacked together into a "sandwich" that is activated by moisture.

TABLE 1

Blue Enzyme/Substrate Layer 1

| Reagent | [Stock] | [Final] | Volume |
|---|---|---|---|
| Immobilized LCP/GOX | 4 μM LCP, 4 μM GOX, 4 mg/mL NP pH 10.6 | 387 nM LCP, 387 nM, 387 μg/mL NP pH 10.6 | 483.75 μL |
| KI | 200 mM | 0.3 mM | 7.5 μL |
| KSCN | 20 mM | 0.5 mM | 125 μL |
| CMC (low viscosity) | 4% | 1% | 1250 μL |
| CMC (high viscosity) | 2% | 0.5% | 1250 μL |
| MilliQ water | | | 1884 μL |
| Blue food coloring | | | 50 μL |

TABLE 2

Yellow Glucose/Substrate Layer 2

| Reagent | [Stock] | [Final] | Volume |
|---|---|---|---|
| β-D-glucose | 500 mM | 50 mM | 500 μL |
| KI | 200 mM | 0.3 mM | 7.5 μL |
| KSCN | 20 mM | 0.5 mM | 125 μL |
| CMC (low viscosity) | 4% | 1% | 1250 μL |
| CMC (high viscosity) | 2% | 0.5% | 1250 μL |
| MilliQ water | | | 1868 μL |
| Yellow food coloring | | | 50 μL |

TABLE 3

Blue Negative Control/Substrate Layer 1

| Reagent | [Stock] | [Final] | Volume |
|---|---|---|---|
| KI | 200 mM | 0.3 mM | 7.5 μL |
| KSCN | 20 mM | 0.5 mM | 125 μL |
| CMC (low viscosity) | 4% | 1% | 1250 μL |
| CMC (high viscosity) | 2% | 0.5% | 1250 μL |
| MilliQ water | | | 1 μL |
| Blue food coloring | | | 50 μL |

In the dry form, the assembly was stable and non-reactive. Upon hydration, however, the substrates ($O_2$, Glucose, KI and KSCN) diffused to the immobilized enzymes. The water-activated assembly combined all the components for bactericide activity against *E. coli* and *Xanthomonas* cultures on Petri dishes.

Figure 4A:
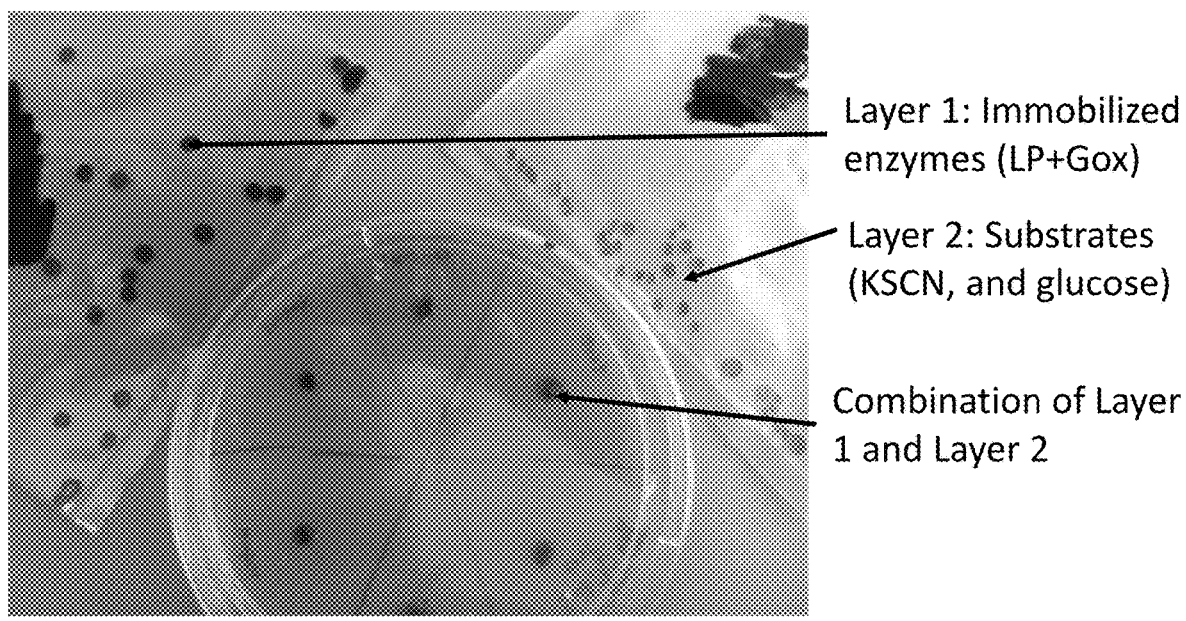
Figure 4B:
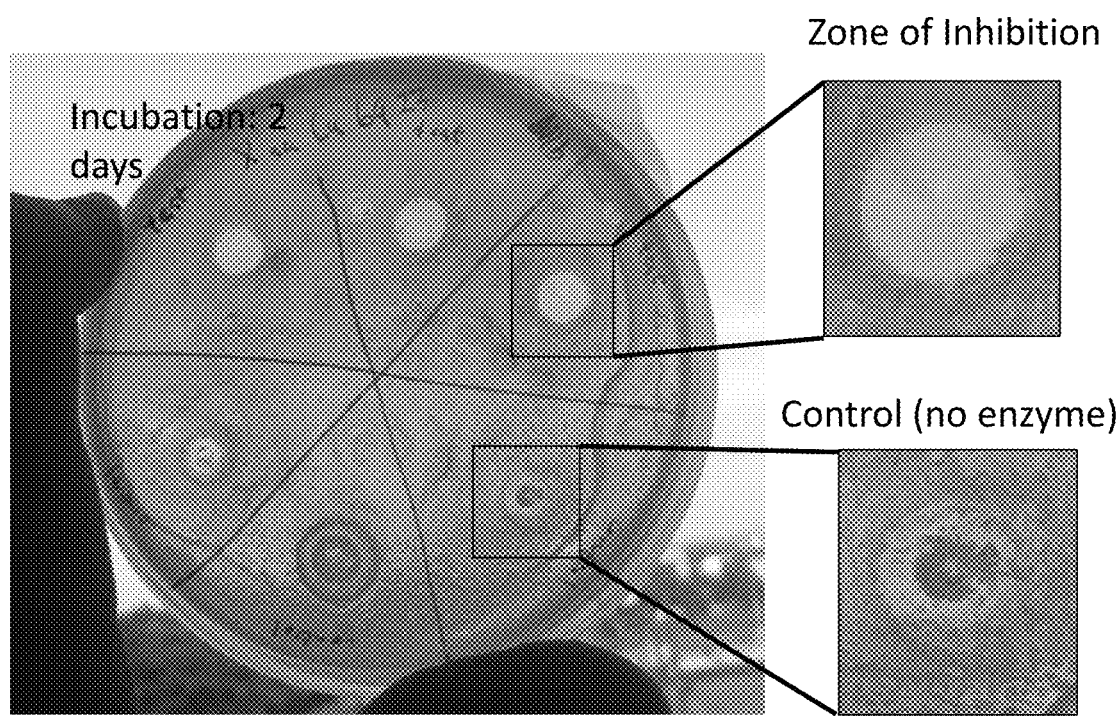

The efficacy of the water-activated formulation against plant pathogens was determined with a method similar to an antibiotic disk diffusion assay. In a disk diffusion assay, small paper disks, soaked in a known concentration of an antimicrobial substance, are placed on a microbial culture agar plate that is then incubated to form a lawn. The size of the zone of growth inhibition can be correlated to the magnitude of the antimicrobial effect of a particular antimicrobial substance against a particular microbe. The layers 1 and 2 were placed on top of each other on lima bean agar freshly inoculated with *Xanthamonas aa* CU6923 (FIG. 4A). The plate was then incubated for 24 h at room temperature. The negative controls that contained no enzyme exhibited no clearance. In contrast, the disks with the immobilized enzymes killed or prevented the growth of *Xanthomonas* as shown by approximately 1 cm clear zones without bacterial growth. Total inhibition of bacterial growth was observed after 24 H and for up to 5 weeks with the enzyme containing formulae. (FIG. 4B). Similar results were found for *E. coli* cultures on Mueller-Hinton Agar, though with smaller and less distinct clearance zones. This may be because *E. coli* is a catalase (+) organism. It may have consumed some of the hydrogen peroxide produced during the reaction resulting in lower and slower hyporadical production by the LCP/GOX system. Thus, Catalase (+) organisms may require higher concentrations of enzymes and substrates.

Example 3

LP/GOX Seed Coating

Seeds are coated with the antimicrobial compositions disclosed herein in a sequential 2 layer system. The concentration of polymer may vary based on the thickness of the coating required. The concentration of the immobilized enzyme may vary based on the efficacy and duration of the antimicrobial activities desired.

The solid antimicrobial LP/GOX assembly was shown to be plant safe according to the following protocol: 1 mL of Yellow Glucose/substrate mix was combined with 500 µL Blue Enzyme/substrate mix. The same was done with 1 mL Yellow and 500 µL Blue Control. The mixtures were vortexed. Using forceps, 20 tomato seeds were each dipped into the Enzyme and Control mixtures and allowed to dry overnight. The seeds were then placed on damp filter paper at the bottom of an empty sterile culture plate marked in three sections: Coated Enzyme+, coated Enzyme-, Uncoated. After 7 days, the seeds were checked for germination.

Figure 5:
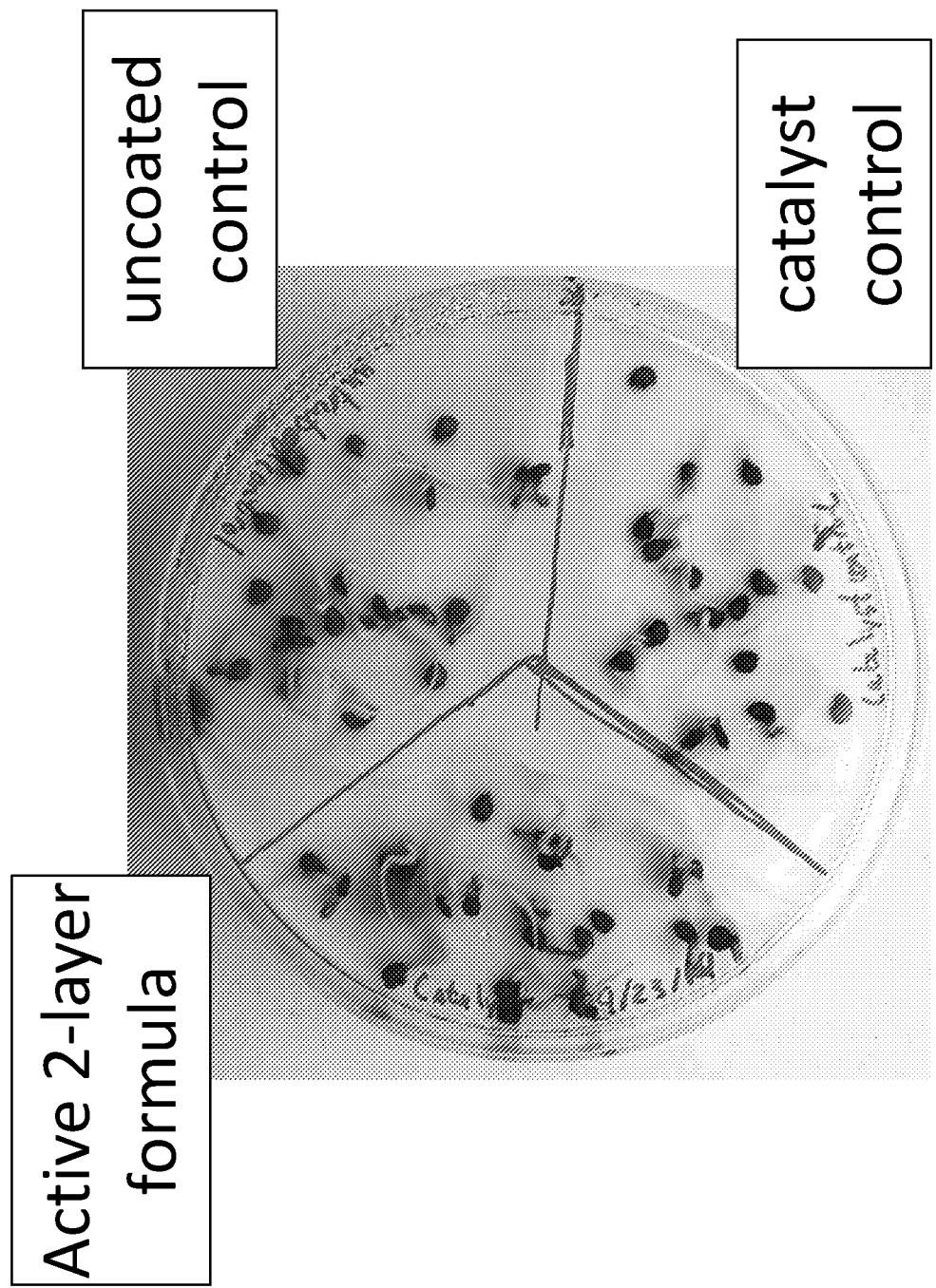

The enzyme coatings did not inhibit seed germination after 7 days (FIG. 5). The test and control seeds showed 85% germination. Using wheat in the same assay, the germination rate was 100% (data not shown).

In an example for small seed batches, 1 g of seeds are soaked first for 1 min in 10 ml of a layer 1 formula and dried at a low temperature (e.g., about 40° C.) in a vacuum oven. The dried seeds are then dipped in a layer 2 formula and dried at a low temperature (e.g., about 40° C.) in a vacuum oven. This coating method may be used to optimize the formulae for enzymes, reagents and viscosity. The viscosity is related to the amount of polymer that is left on the seeds after drying.

Figure 6:
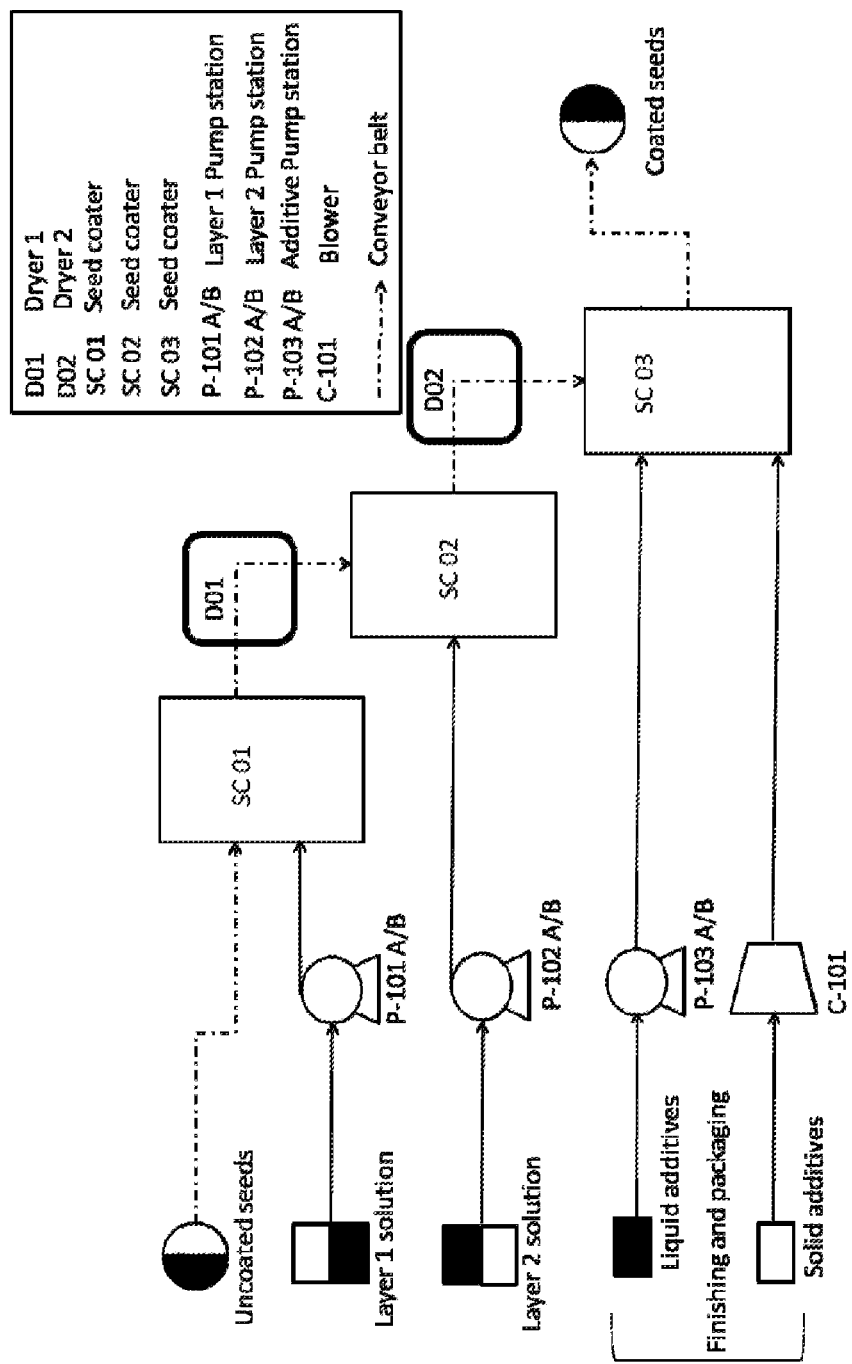

In an example for larger batches of seed coating (e.g. greater than 1 g, 10 g, or up to 5 kg or more of seeds), a commercial seed coating machine as known in the art may be used. (FIG. 6.) Exemplary seed coating machines may comprise a vertical cylindrical stator and a horizontal, plate-shaped rotor. The rotor rotates the seed, thus forcing it to rise up through the stator, where they lose speed and spiral down again into the middle of the mixing chamber. The middle of the mixing chamber may comprise a rotating spinning disc that ensures the dispersion of the coating materials. Alternatively for low-viscosity solutions, a spraying nozzle to may spray or nebulize the solutions.

In some embodiments, a mixing phase and drying phase may be utilized. First, the solution containing the enzymes is spread on the spinning seed at about a 1-to-2 ratio (enzyme weight:seed weight). A dry air jet drier may be used to dry the seeds. The time required for the drying may vary based on the quantity of seeds and water to evaporate. When the seeds are fully dried, the solution of layer 2 containing the glucose, other substrates, or other reagents is spread on the spinning seeds in about a 1-to-2 ratio (solution weight: seed weight). A dry air jet drier may be used to dry the rotating seeds. The ratios of layer solutions to seeds may be varied as is known in the art to optimize the resultant seed coatings.

For larger batches of more than 10 kg, sequential seed coaters may be used to facilitate the drying of the seeds in between coatings. Seeds are moved from one coater to another via mechanical means known in the art (e.g. conveyor belts). The time used for said movement may be used for drying prior to the next coating (FIG. 6)

A person of skill in the art would recognize that additional layers or components may be added to the coated seeds at any time during the process so long as it does not prevent activation of the antimicrobial compositions. Additional coating steps can include other organic, inorganic and biological additives such as drying agents (e.g. talc), coloring agents (e.g. dyes), pesticides (e.g. insecticides), plant-beneficial bacteria (e.g. Plant Growth Promoting *Rhizobacteria* spores), or other chemicals (e.g. fungicides, fertilizers, macronutrients and micronutrients). Priming of the seeds (e.g. prehydration) can be optimized by controlling the quantity of water allowed to permeate in the seeds during the coating of the first layer.

The efficacy of the seed coating is tested in growth chambers where coated seeds are grown in the presence of target pathogens (e.g. *xanthomonas* for tomato) on a minimal water agar. The coated seeds are placed to germinate on the agar surface inoculated with the pathogen. The diameter of the zone of inhibition around the seed shows the efficacy of the formula.

Alternatively, the seeds are grown in about 10 g of inoculated soil (about $10^5$ pathogen cells per g of soil) in a controlled growth chamber (14 h daylight, 10 h night, 60% Humidity, 22° C.). Soil efficacy is tested by measuring the emergence of seedlings (germination rate), the presence or occurrence of the pathogen in the plants, and post germination mortality.

Example 4

LP/GOX Animal Bedding Coating

Figure 7:
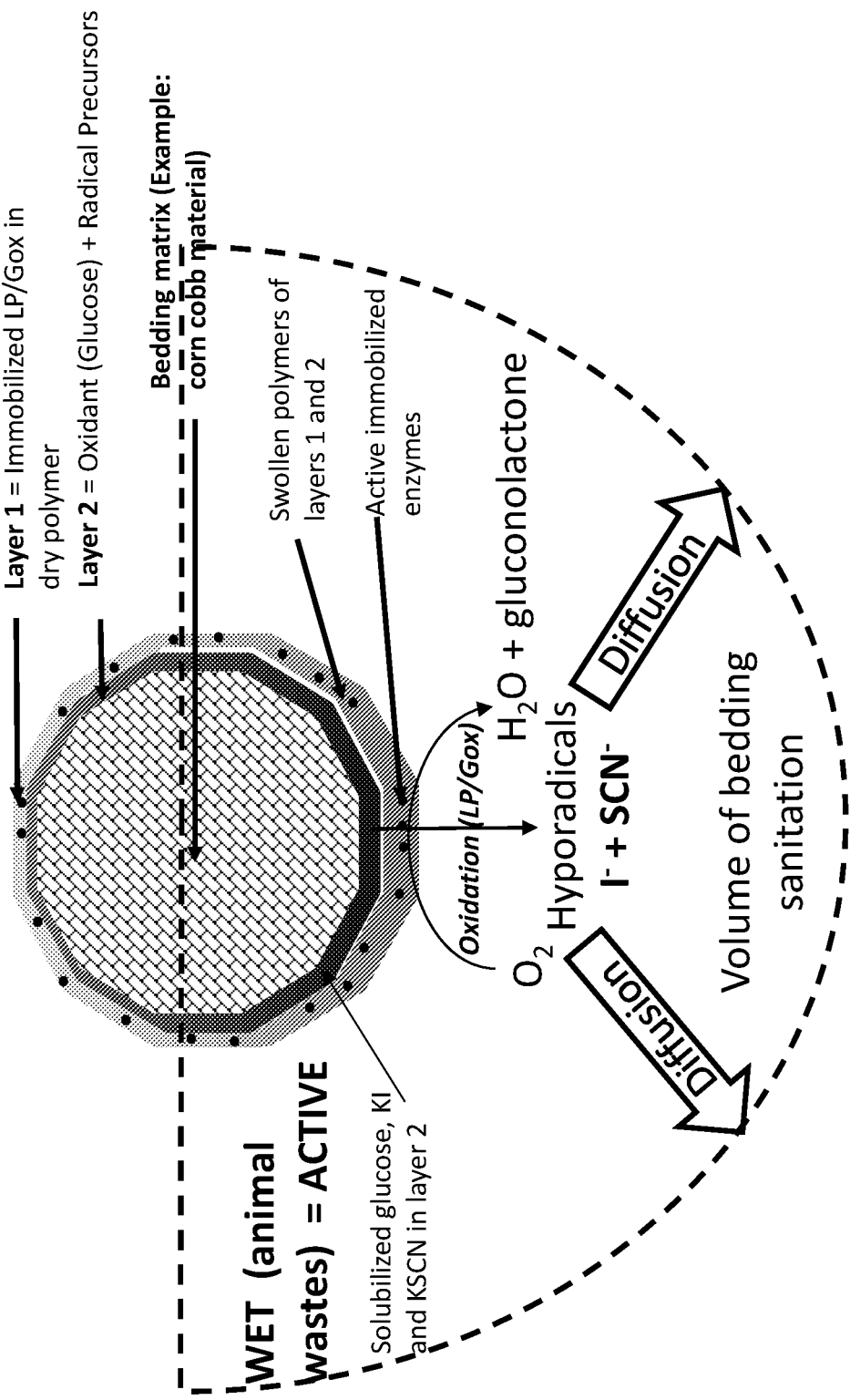

In one example of the invention, animal bedding is coated with the solid antimicrobial assemblies disclosed herein using ground corn cobs (FIG. 7, Green Products Company, Conrad, Iowa). The "wood-like" material can absorb its own weight in water while the softer pith and shaft can absorb up to 4.5-fold their weight in water. The material is mechanically resistant, biodegradable, compostable, and renewable. Particles below 3.2 mm in diameter (e.g. GreenTru⅛") are used primarily for small animal bedding. It is made from the woody-ring portion and has good absorption features. GreenTru 1020 corncob is currently used for "carrier" applications where large quantities of corncob particles are needed (pesticides and fertilizers).

The corn cob particles are soaked with glucose (100 mM), KI and KSCN (0.5 mM each) at 4° C. and 0.5% polymer at 50% of water holding capacity (WHC) for 24 hours and then air dried between 50 and 100° C. to 10% moisture. The "loaded" particles act as a reservoir for the reaction reagents. The loaded particles are dipped in the coating formula containing the immobilized enzyme system and the optimal CMC concentration as disclosed herein. The coated particles are allowed to dry for 24 hours.

Efficacy of the functionalized bedding particles is shown in liquid and on solid bacteria culture. For the solid cultures, 10 particles of coated material are placed on Petri dishes inoculated with the target bacteria. The particles are activated with 10 µl of water or artificial cow urine (2% urea, pH 6). The diameter of the non-growth zone (ring) around the particles is measured for inhibition efficiency.

In solution, 1 particle is added to 1 ml bacteria culture ($10^5$, $10^6$, $10^7$ and $10^8$ bacteria). The percentage of live and dead cells is measured as previously described above with the LIVE/DEAD® kit at 5 minutes, 1 hour, 24 hours, and 48 hours.

Figure 8:
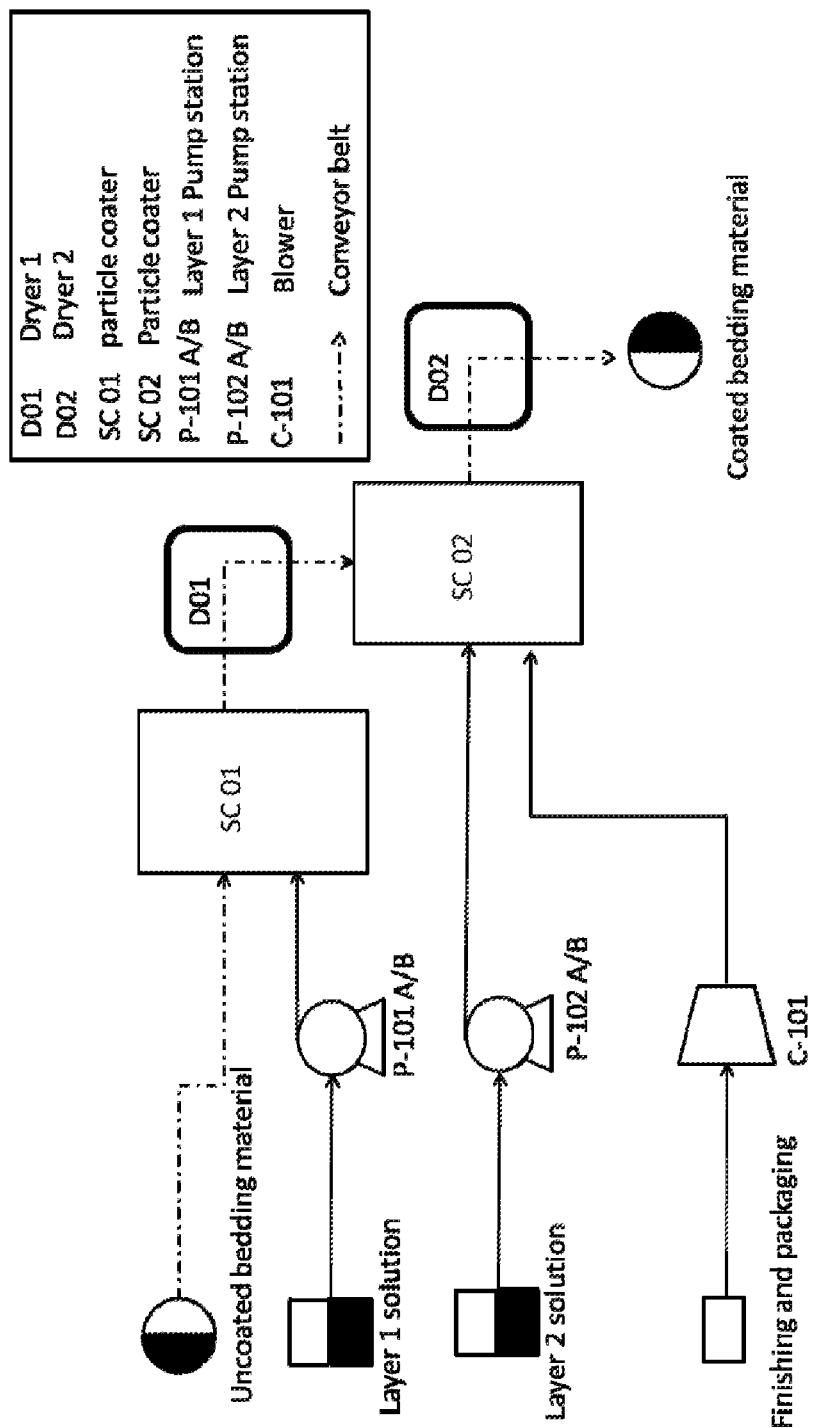
Figure 9:
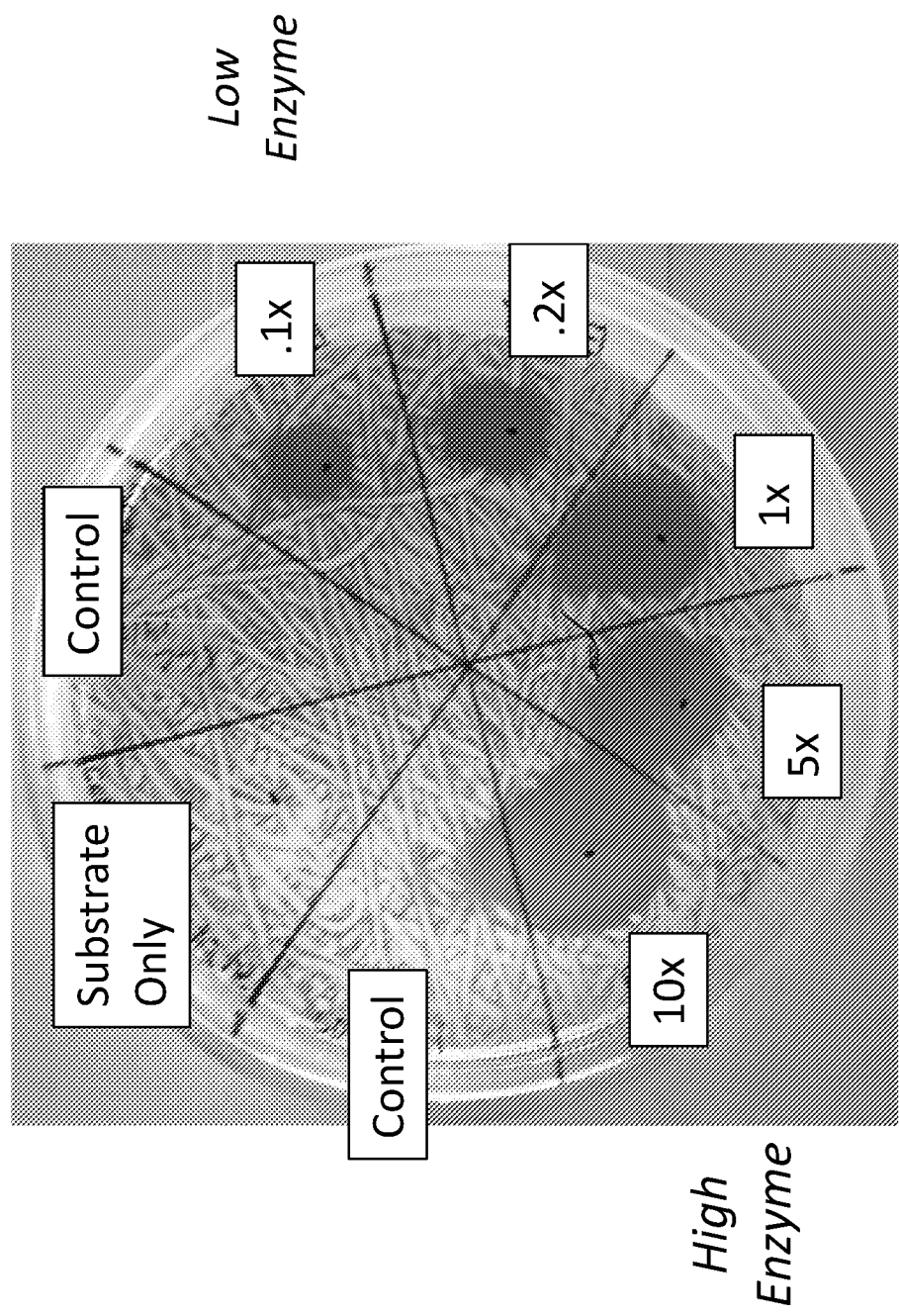
Figure 10A:
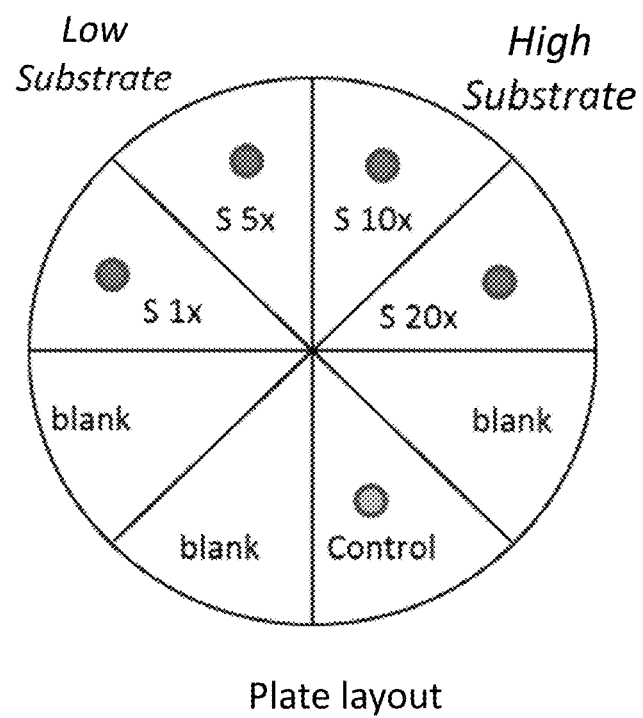
Figure 10B:
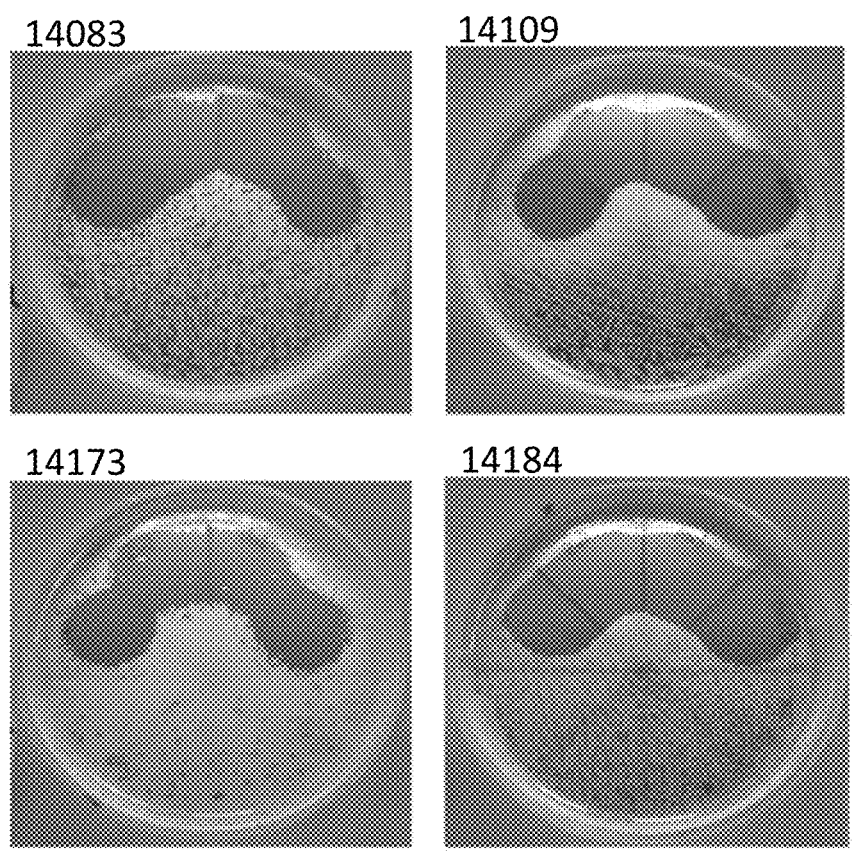
Figure 11:
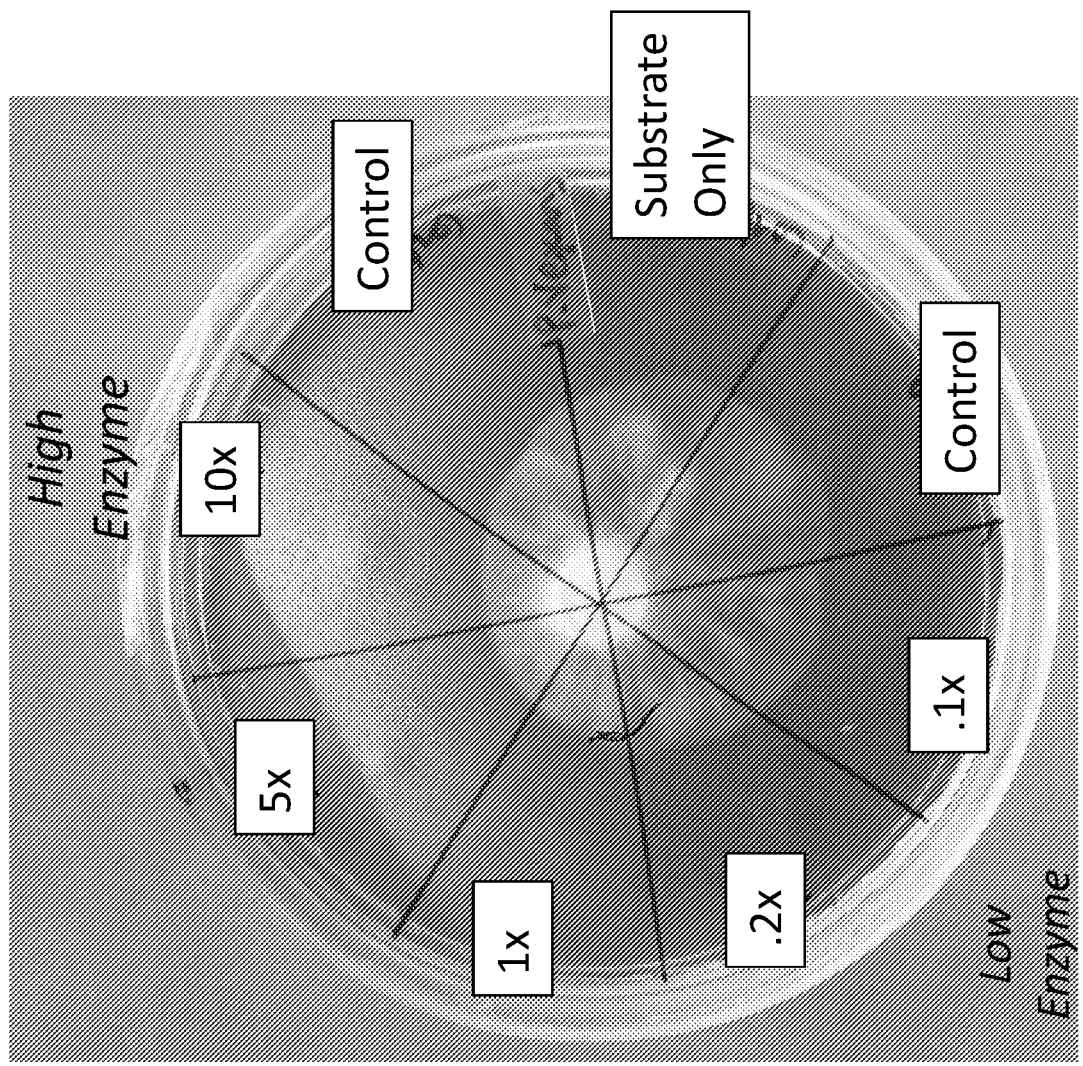
Figure 12A:
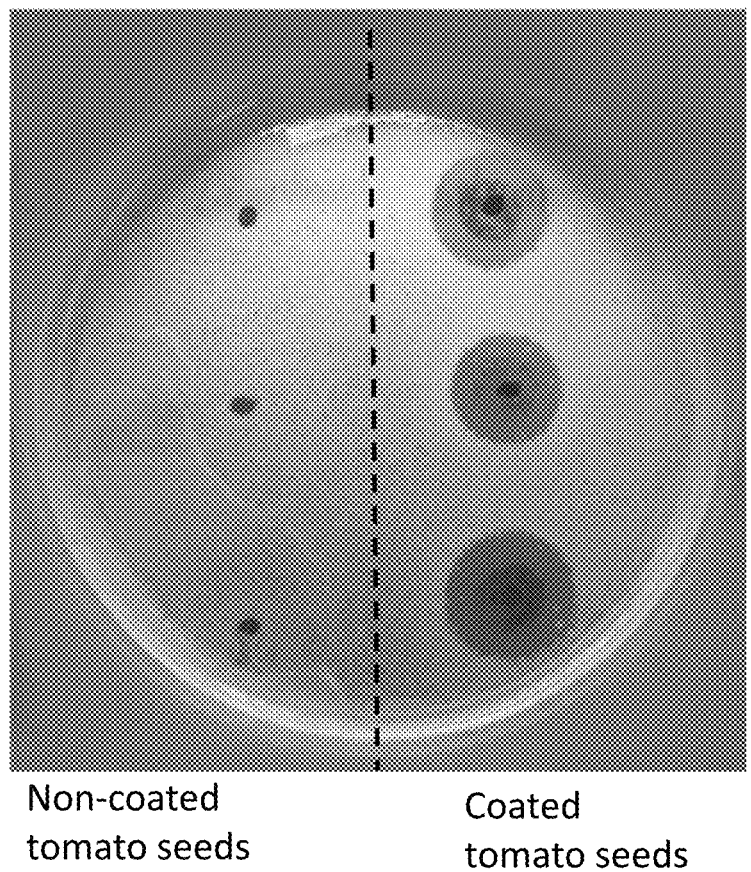
Figure 12B:
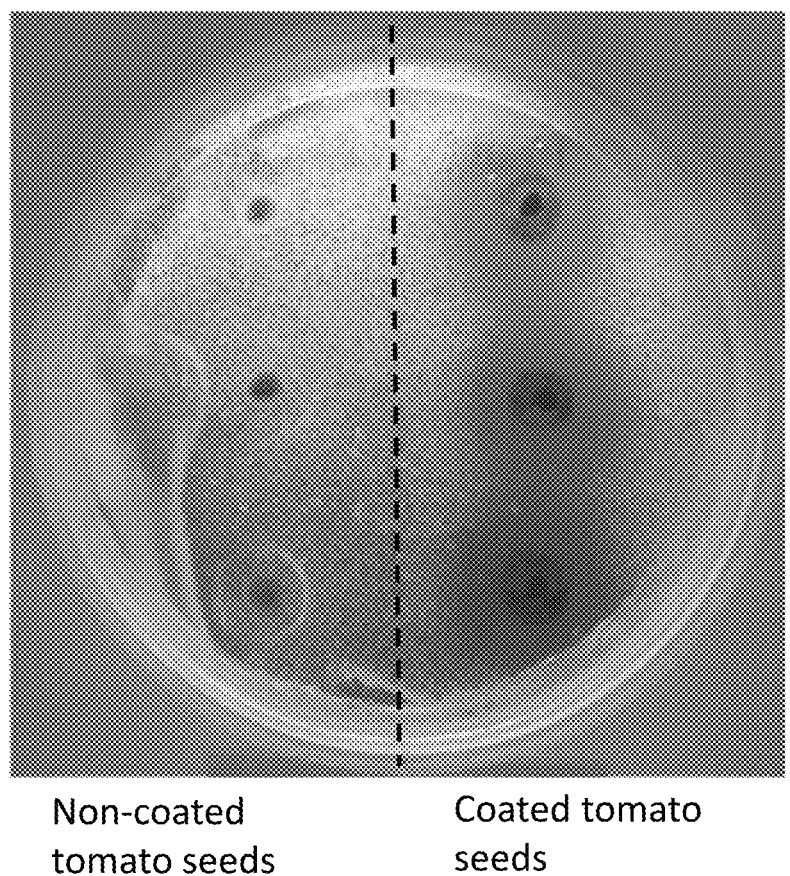
Figure 13:
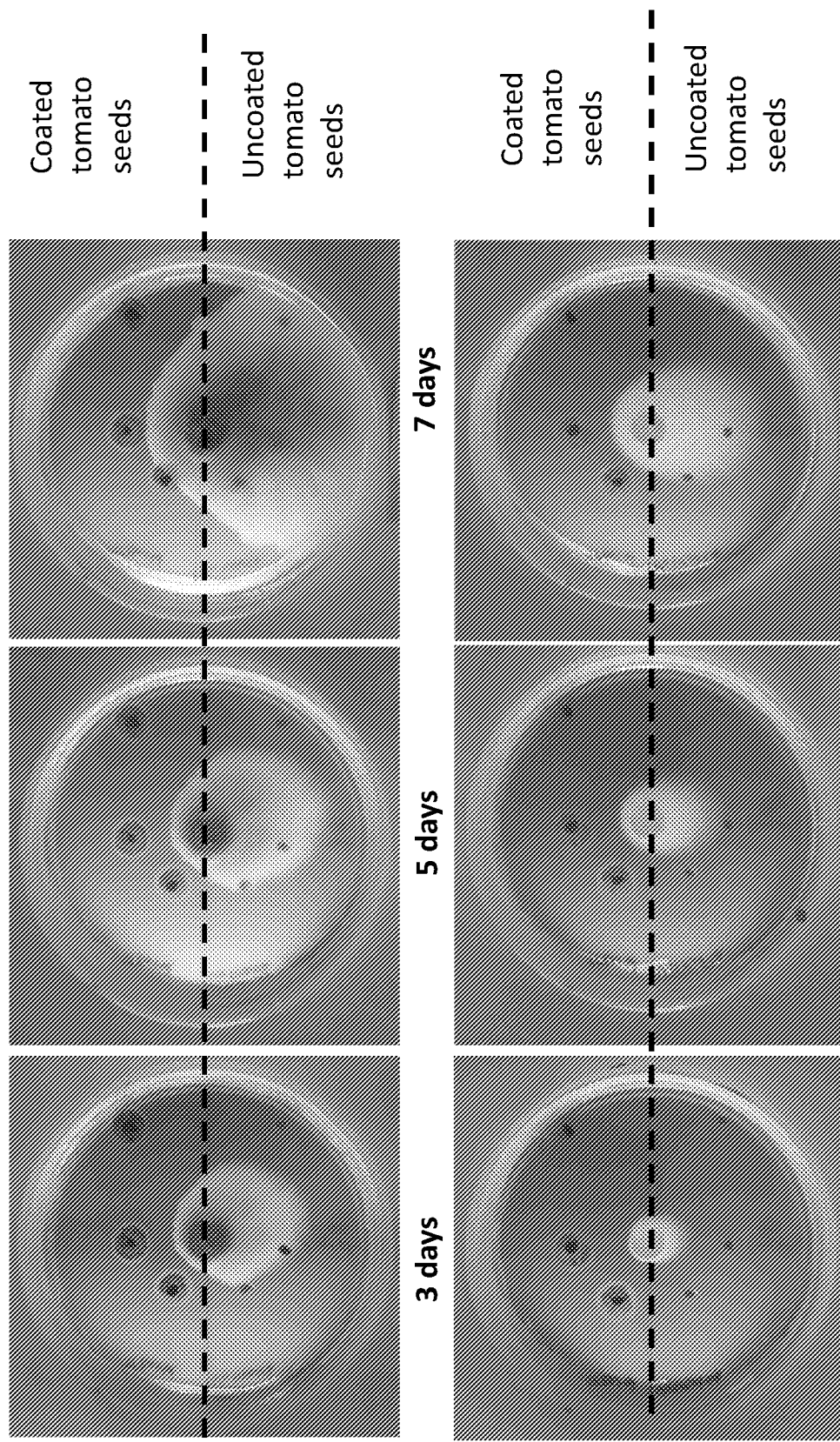

For larger batches of material coating (e.g. greater than 1 g, 10 g, or up to 5 kg or more of corn cob material), commercial coating machines as described above may be used. (FIG. 8.) First, the material is sprayed with the solution containing the glucose (50 to 100 mM) and reagents (0.5 mM KSCN and KI each) and 0.5% polymer (CMC) in a 1:1 ratio (1 g of material for 1 g of solution). The material is then dried at a temperature of between 50 and 100° C. In some embodiments, an air jet stream may be used. The solution containing the immobilized enzymes is then spread on the material at a 1-to-2 ratio (solution weight:material weight). For example, this may be 2% polymer and 0.5 mM of KSCN and KI. The concentration of polymer varies based on the thickness of the coating required. The concentration of the immobilized enzyme varies based on the efficacy and duration of the antimicrobial activities desired. The enzyme concentrations are optimized for bedding and pathogens. The final materials are dried to a moisture content of about 10% or less. The time required for the drying varies based on the quantity of material and water to evaporate.

For larger batches of more than 10 kg, sequential particle coaters may be used to facilitate the drying of the seeds in between coatings. Seeds are mechanically moved from one coater to another (e.g. via conveyor belts) so that drying time is provided prior to the next coating.

Example 5

Bovine Lactoperoxidase and *Aspergillus niger* Glucose Oxidase Seed Coatings In another example of the invention, LP/GOX was formulated at a ratio of 1:10 LP to GOX. The GOX was from *Aspergillus niger* (Sigma Aldrich, St. Louis, Mo., Cat. No. G7141). The LP was from bovine milk (Sigma Aldrich, St. Louis, Mo., Cat. No. 61328). Thus, a 1× composition of enzyme was formulated with 38.7 nM lacto-peroxidase and 387 nM glucose oxidase and 300 μg/ml NPs. The composition also had 0.3 mM of KI and 0.5 mM of $NH_4SCN$. The enzymes were first co-immobilized. Briefly the enzymes were mixed together then added to sonicated NP (1 min at 40% power) to a final volume of 1 ml. The tubes are then shaken for 1 hour at 1100 rpm.

The immobilized enzyme assemblies were made at 0.1×, 0.2×, 1×, 5×, and 10× concentrations by placing 20 μl dots on agar plates. The quantity of carboxymethyl-cellulose polymer (CMC) in the assemblies was kept constant at 4% and the formula was colored blue with food coloring (FD&C Blue 1 and red 40, 10 μl per ml). Each dot contained 20 μl of formulation dried overnight at room temperature or under vacuum for 1 hour.

A 1× substrate formulation contained 4% CMC, 0.3 mM of KI, 0.5 mM of $NH_4SCN$ and 50 mM of Glucose. The different substrate concentrations (1×, 5×, 10×, and 20×) were analyzed by increasing the concentration of the substrate while the quantity of CMC was kept constant at 4%. The formula was colored yellow with food coloring (FD&C yellow 5, 10 μl per ml). Each dot contained 20 μl of formulation dried overnight at room temperature or under vacuum for 1 hour.

The enzyme assemblies efficiently inhibited bacterial growth. Bacteria were grown on LB media (10 g/L tryptone, 5 g/L yeast extract, 10 g NaCl/L) in liquid culture or solid agar plates (agar 15 g/L). The formulae were tested on field isolates of *Xanthomonas campestris* pathovars, *Pseudomonas syringae* var. *tomato*, and *Clavibacter michiganensis*. The bacteria (48 hours liquid culture adjusted to $10^6$ bacterial per ml) were plated onto agar plates at approximately $6.6 \times 10^5$ bacteria per plate using a glass bead procedure to form a bacterial lawn. After inoculation, dry disks containing the enzymes were placed on the surface and dry disks with the substrate were added on top of them. As the CMC rehydrated, the substrates diffused, including the food coloring, so that the disk turned green. Alternatively, coated seeds were placed at the surface of the agar. The plates were incubated at room temperature for 48 to 96 hours and the plates were done in triplicate. As shown in FIG. 9, *X. campestris* was efficiently inhibited by the enzyme assemblies in a dose-dependent manner. The halo of inhibition increased with the concentration of enzyme. Similarly, FIGS. 10A and 10B show inhibition of *X. campestris* even at the lowest substrate concentrations.

The enzyme assemblies efficiently inhibited fungal growth. Fungi were grown on potato dextrose agar. Fresh plates were inoculated with one plug (7 mm diameter) of the fungal strain centered on the plate. After inoculation of the plates, dry disks containing the enzyme dilutions were added to the surface of the agar and dry disks with the substrate were added on top of them. As the CMC rehydrated, the substrates diffused, including the food coloring, so that the disk turned green. The disks were added at the same distance from the inoculum to observe the growth of the mycelium. FIG. 11 shows a dose-dependent inhibition of *Pythium vexans* with increasing enzyme concentrations The enzyme assemblies efficiently protected tomato seeds. Tomato seeds (var. Rutgers) were coated manually by first dipping the seeds in the enzyme formulation, vacuum drying the first layer, dipping the seeds in the substrate formulation, and vacuum drying the seeds a second time at room temperature. Between 10 and 13 μl of each solution was deposited on the seeds at each coating step. The seeds were allowed to dry overnight and stored at 4° C. until further use. FIGS. 12A and 12B show that the coated seeds were efficiently protected from *Pseudomonas syringae* and *Clavibacter michiganensis* infections.

In a further demonstration of the invention, coated seeds were placed at different distances from inoculum plugs containg *Fusarium equiseti* and *Fusarium oxysporum*. *Pythium vexans* and *Rhizoctonia Solani* were also analyzed (data not shown). The fungi were incubated at room temperature and the plates were done in triplicate. FIG. 13 shows the distance-dependent inhibition of *Fusarium* after 3, 5, and 7 days.

Discussion. The formulations containing co-immobilized lactoperoxidase and glucose oxidase efficiently protect agricultural materials against *Xanthomonas, Pseudomonas, Clavibacter, Pythium*, and *fusarium*. The control indicated that the dyes or substrates alone had no effect on the bacteria or fungi. A strong bactericide effect was observed for all bacteria with a clear sanitation zone formed by the hydrated polymers (FIGS. 9-11) or formed around the coated seeds (FIGS. 12-13). The area of sanitation was shown to be mostly enzyme concentration dependent (FIG. 2). The concentration of substrates had little effect on short-term sanitation but might be determinant in maintaining the effects for longer periods of time. Immobilized glucose oxidase alone also had a modest level of bactericidal activity due to the production of hydrogen peroxide. The antibacterial effect, however, was significantly increased by the presence of co-immobilized bovine lactoperoxidase.

In the case of the fungal pathogens *Fusarium oxysporum, Fusarium equiseti, Fusarium graminearum* and *Pythium vexans*, a very strong negative chemorepulsion was observed. As shown in FIGS. 11 and 13, the growth of the mycelium was anisotropic and slower towards the area containing the enzyme formulations (dots or coated seeds). The protection was observed for more than 2 weeks with *Fusarium* and *Pythium*. No significant effect on *Rhizoctonia solani* was observed in the range of enzymes and substrate tested.

Because the enzymes were highly effective even at the 0.1× concentration, approximately 1 g of bovine lactoperoxidase can be used to coat and protect 30.3 million tomato seeds and 1 g of glucose oxidase 3.03 million tomato seeds. Similarly, 1 kg of potassium iodide and ammonium thiocyanate are enough to coat and protect 912 million and 1.193 billion seeds, respectively. Because a liter of bovine milk contains approximately 33 mg of lactoperoxidase, one liter of milk can be processed to extract enough lactoperoxidase to protect approximately 1 million tomato seeds against fungal and bacterial pathogens. On average, one cow produces about 20 liters of milk per day. Each liter contains enough lactoperoxidase to coat about 20 million tomato seeds. The composition can be used to coat other seeds; the quantity of solution to be used per seed is proportional to the surface area of the seed compared to the quantities used for tomato seeds All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A liquid antimicrobial composition, comprising;
   a. a polymeric water-solvatable matrix formulated with self-assembled mesoporous aggregates of magnetic nanoparticles comprising a free radical producing enzyme; and
   b. a segregated component having a substrate for said free radical producing enzyme and a hydrogen peroxide source;

wherein said polymeric water-solvatable matrix causes said composition to be essentially inactive and stable, wherein mixing said polymeric water-solvatable matrix and segregated component activates said composition and results in said hydrogen peroxide source acting as a substrate for said free radical producing enzyme, and wherein free radicals are produced having a microbiostatic or a microbiocidal activity, wherein said polymeric water-solvatable matrix is in the form of a coating.

2. The liquid antimicrobial composition of claim 1, wherein said matrix further comprises a hydrogen peroxide producing enzyme and said hydrogen peroxide source is a substrate for said hydrogen peroxide producing enzyme.

3. The antimicrobial composition of claim 1, wherein said activity is bacteriostatic or bacteriocidal.

4. The antimicrobial composition of claim 1, wherein said activity is viricidal.

5. The antimicrobial composition of claim 1, wherein said activity is fungicidal.

6. A liquid pesticide product comprising the antimicrobial composition of claim 1.

7. A method of reducing or eliminating microbial pest growth comprising spraying a substance with the liquid antimicrobial composition of claim 1.

8. The antimicrobial composition of claim 1, wherein said mesoporous aggregates of magnetic nanoparticles have an iron oxide composition.

9. The antimicrobial composition of claim 1, wherein said mesoporous aggregates of magnetic nanoparticles have a magnetic nanoparticle size distribution in which at least 90% of magnetic nanoparticles have a size of at least 3 nm and up to 30 nm, and an aggregated particle size distribution in which at least 90% of said mesoporous aggregates of magnetic nanoparticles have a size of at least 10 nm and up to 500 nm.

10. The antimicrobial composition of claim 2, wherein said hydrogen peroxide generating enzyme is an oxidase.

11. The antimicrobial composition of claim 10, wherein said oxidase is glucose oxidase or alcohol oxidase.

12. The antimicrobial composition of claim 2, wherein said substrate for said hydrogen peroxide generating enzyme is β-D-Glucose or an alcohol.

13. The antimicrobial composition of claim 1, wherein said free radical producing enzyme is a peroxidase.

14. The antimicrobial composition of claim 13, wherein said peroxidase is a lactoperoxidase.

15. The antimicrobial composition of claim 13, wherein said peroxidase is myeloperoxidase, eosinophil peroxidase, or thyroid peroxidase.

16. The antimicrobial composition of claim 13, wherein said substrate for said peroxidase is thiocyanate, iodide, or bromide.

17. The antimicrobial composition of claim 1, wherein said free radical generating enzyme produces hypothiocyanite, hypoiodite, or hypobromite.

18. The antimicrobial composition of claim 1, further comprising a cellulase enzyme.

19. The antimicrobial composition of claim 18, wherein said cellulase enzyme is an exocellulase or an endocellulase.

* * * * *